US009034761B2

United States Patent
Lansalot-Matras et al.

(10) Patent No.: US 9,034,761 B2
(45) Date of Patent: May 19, 2015

(54) HETEROLEPTIC (ALLYL)(PYRROLES-2-ALDIMINATE) METAL-CONTAINING PRECURSORS, THEIR SYNTHESIS AND VAPOR DEPOSITION THEREOF TO DEPOSIT METAL-CONTAINING FILMS

(75) Inventors: Clément Lansalot-Matras, Seoul (KR); Andrey V. Korolev, Germantown, WI (US)

(73) Assignees: L'Air Liquide, SociétéAnonyme pour l'Etude et l'Exploitation des Procédés Georges Claude, Paris (FR); American Air Liquide, Inc., Houston, TX (US)

( * ) Notice: Subject to any disclaimer, the term of this patent is extended or adjusted under 35 U.S.C. 154(b) by 0 days.

(21) Appl. No.: 14/159,815

(22) PCT Filed: Jun. 29, 2012

(86) PCT No.: PCT/US2012/044950
§ 371 (c)(1),
(2), (4) Date: Feb. 26, 2014

(87) PCT Pub. No.: WO2013/015947
PCT Pub. Date: Jan. 31, 2013

(65) Prior Publication Data
US 2014/0179105 A1    Jun. 26, 2014

Related U.S. Application Data

(60) Provisional application No. 61/510,857, filed on Jul. 22, 2011.

(51) Int. Cl.
*H01L 21/44* (2006.01)
*H01L 21/285* (2006.01)
(Continued)

(52) U.S. Cl.
CPC .......... *H01L 21/28506* (2013.01); *C07F 15/04* (2013.01); *H01L 21/76838* (2013.01)

(58) Field of Classification Search
USPC .......... 252/519.1; 257/E21.269, E21.274, 257/E21.586; 420/434, 435, 441, 463; 427/125, 248.1; 438/680, 681
See application file for complete search history.

(56) References Cited

U.S. PATENT DOCUMENTS

| 5,403,620 A | 4/1995 | Kaesz et al. |
| 2005/0220998 A1 | 10/2005 | Chang et al. |
| 2010/0119406 A1 | 5/2010 | Dussarrat et al. |

FOREIGN PATENT DOCUMENTS

WO      WO 98 30609      7/1998

OTHER PUBLICATIONS

Becht, M. et al., "Nickel thin films grown by MOCVD using Ni(dmg)2 as precursor," Journal de Physique IV (1995) C5-465-C5-472.

(Continued)

*Primary Examiner* — Asok K Sarkar
(74) *Attorney, Agent, or Firm* — Patricia E. McQueeney

(57) ABSTRACT

Disclosed are metal-containing precursors having the formula Compound (I) wherein: —M is a metal selected from Ni, Co, Mn, Pd; and —each of $R_{-1}, R_2, R_3, R_4, R_5, R_6, R_7, R_8, R_9$, and $R_{10}$ are independently selected from H; a C1-C4 linear, branched, or cyclic alkyl group; a C1-C4 linear, branched, or cyclic alkylsilyl group (mono, bis, or tris alkyl); a C1-C4 linear, branched, or cyclic alkylamino group; or a C1-C4 linear, branched, or cyclic fluoroalkyl group. Also disclosed are methods of synthesizing and using the disclosed metal-containing precursors to deposit metal-containing films on a substrate via a vapor deposition process.

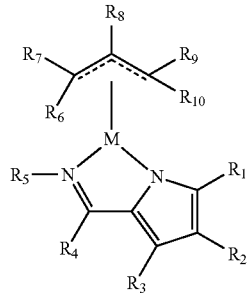

20 Claims, 12 Drawing Sheets

AES of a nickel films grown in PEALD mode at 400°C using allyl pyrroles-2-methylaldiminate nickel(II).

(51) Int. Cl.
C07F 15/04 (2006.01)
H01L 21/768 (2006.01)

(56) References Cited

OTHER PUBLICATIONS

Bellabarba, R.M. et al., "Synthesis of allyl- and aryl-iminopyrrolyl complexes of nickel," Dalton Trans. (2003) 4431-4436.
Brissonneau, L. et al., "MOCVD-processed Ni films from nickelocene. Part I. Growth rate and morphology," Chemical Vapor Deposition 5 (1999) 135-142.
Chung, T.-M. et al., "Volatile nickel aminoalkoxide complexes as liquid precursors for non-volatile memory device of NiO films by ALD," Bull. Korean Chem. Soc. 2011, vol. 32, No. 3, pp. 783-784.
Hitchcock, P.B. et al., "Synthesis and structures of the transition metal(II) β-diketiminates $[ML_2]$ (M=Mn, Fe, Ni, Cu, Pd), $[ML'_2]$ (M-Ni, Cu) and $[M(\eta^3-C_3H_5)L]$ (M=Ni, Pd); L or L'=[{N(SiMe$_3$ or H)C(Ph)}$_2$CH]," Journal of Organometallic Chemistry 694 (2009) 667-676.
Kada, T. et al., "Volatile CVD precursor for Ni film: cyclopentadienylallylnickel," Journal of Crystal Growth 275 (2005) e1115-e1119.
Kang, J.-K. et al., "Metalorganic chemical vapor deposition of nickel films from Ni(C5H5)2,H2," J. mater. Res., vol. 15, No. 8, Aug. 2008, 1828-1833.
Li, B.S. et al., "Direct-liquid-injection chemical vapor deposition of nickel nitride films and their reduction to nickel films," Chemistry of Materials (2010) 22, 3060-3066.
Lim, Z. et al., "Synthesis and characterization of volatile, thermally stable, reactive transition metal amidinates," Inorganic Chemistry (2003) 42, 7951-7958.
Maruyama, T. et al., "Nickel thin films prepared by chemical vapour deposition from nickel acetylacetonate," Journal of Materials Science 28 (1993) 5345-5348.
Musgrave, C.B. et al., "Precursors for atomic layer deposition of high-k dielectrics," Process Gases, Chemicals and Materials Section 7 / FutureFab international 18 (2005) 126-128.
Perez-Puente, P. et al., "Synthesis of 2-(N-arylimino-kN-methyl)pyrrolide-kN complexes of nickel," Journal of Organometallic Chemistry 693 (2008) 3902-3906.
International Search Report and Written Opinion for PCT/US2012/044950, Jan. 24, 2013.

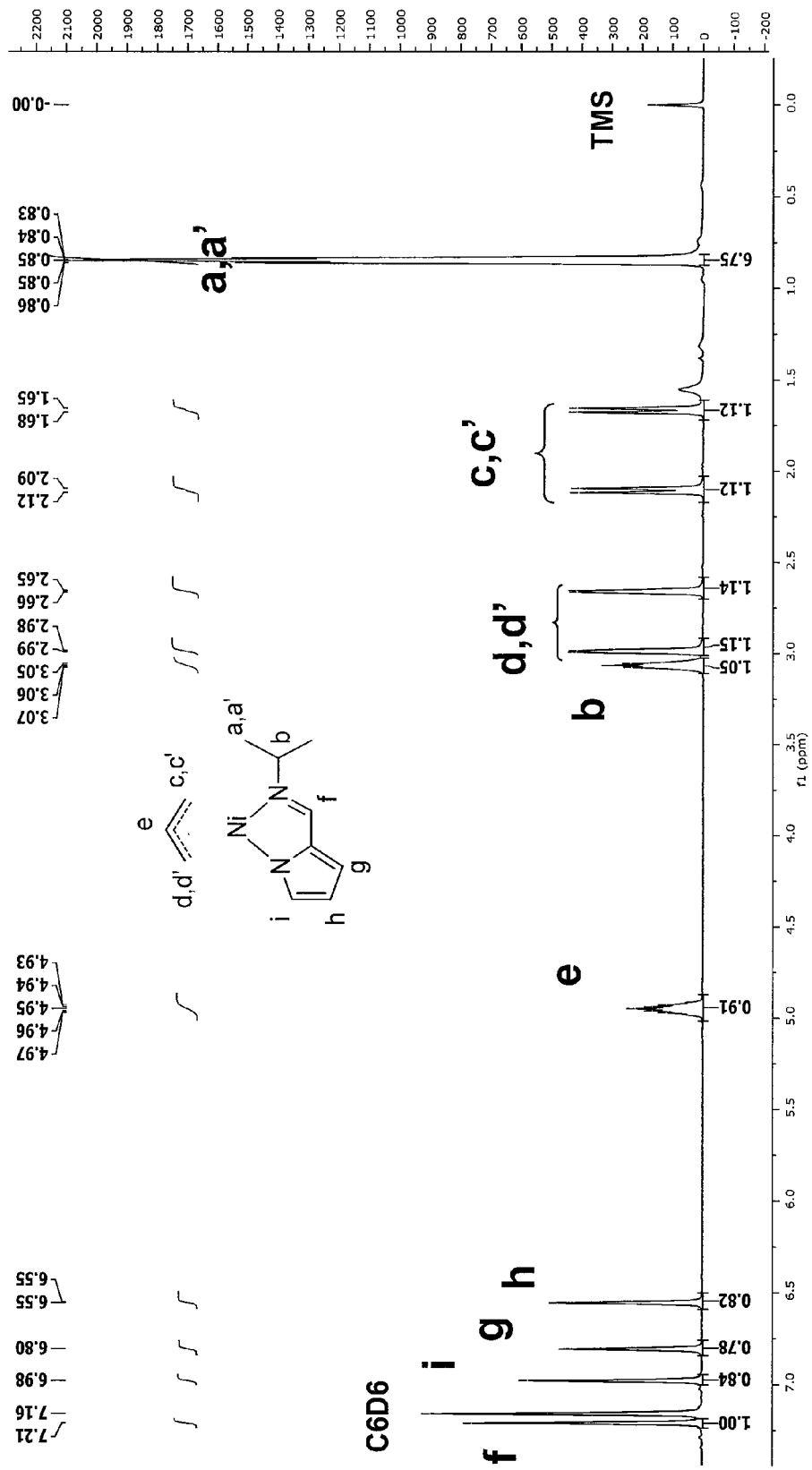
FIG 1: NMR 1H of allyl 2-isopropyliminemethylpyrrolyl nickel(II) in C6D6

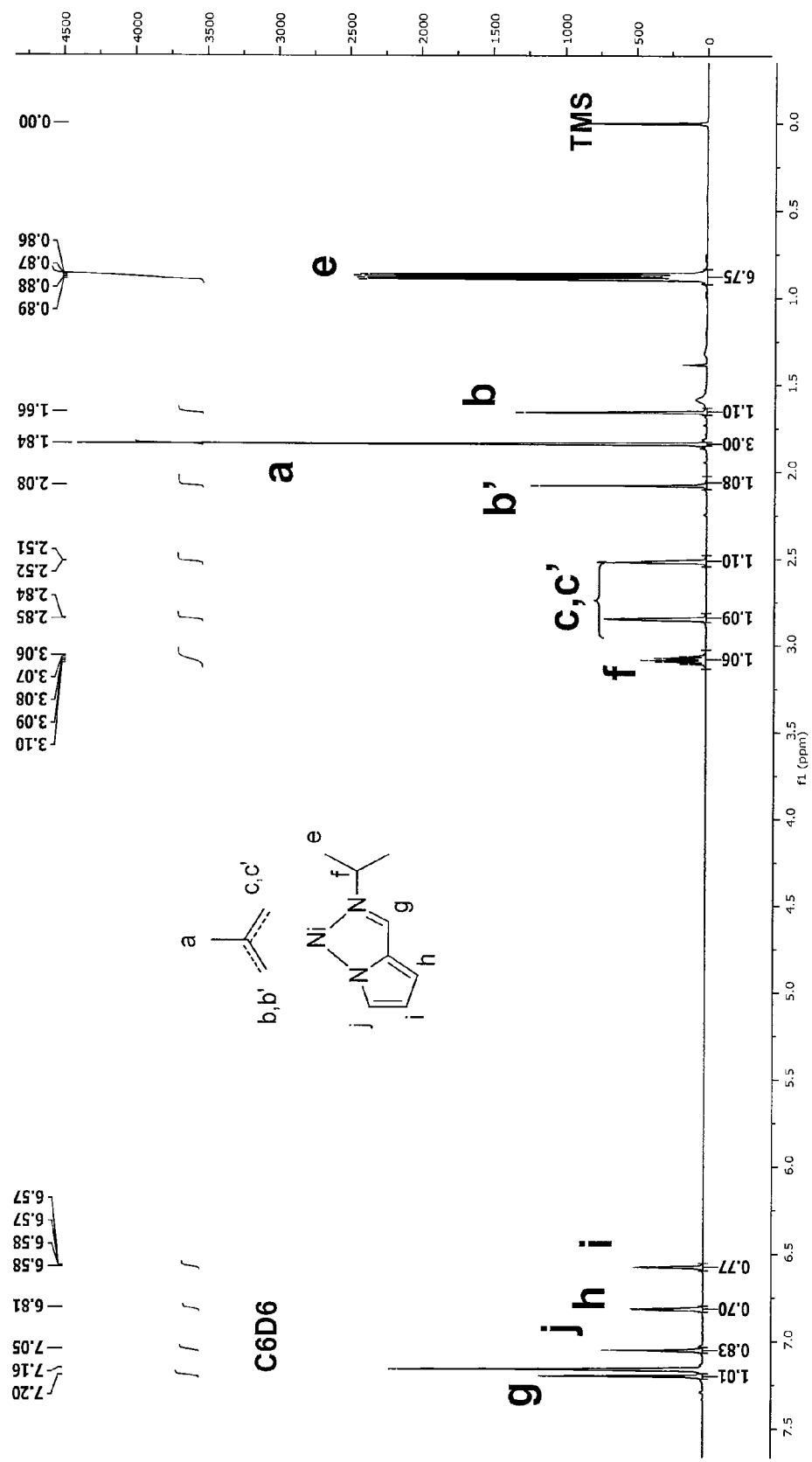
FIG 2 NMR 1H of 2-methylallyl 2-isopropyliminemethylpyrrolyl nickel(II) in $C_6D_6$

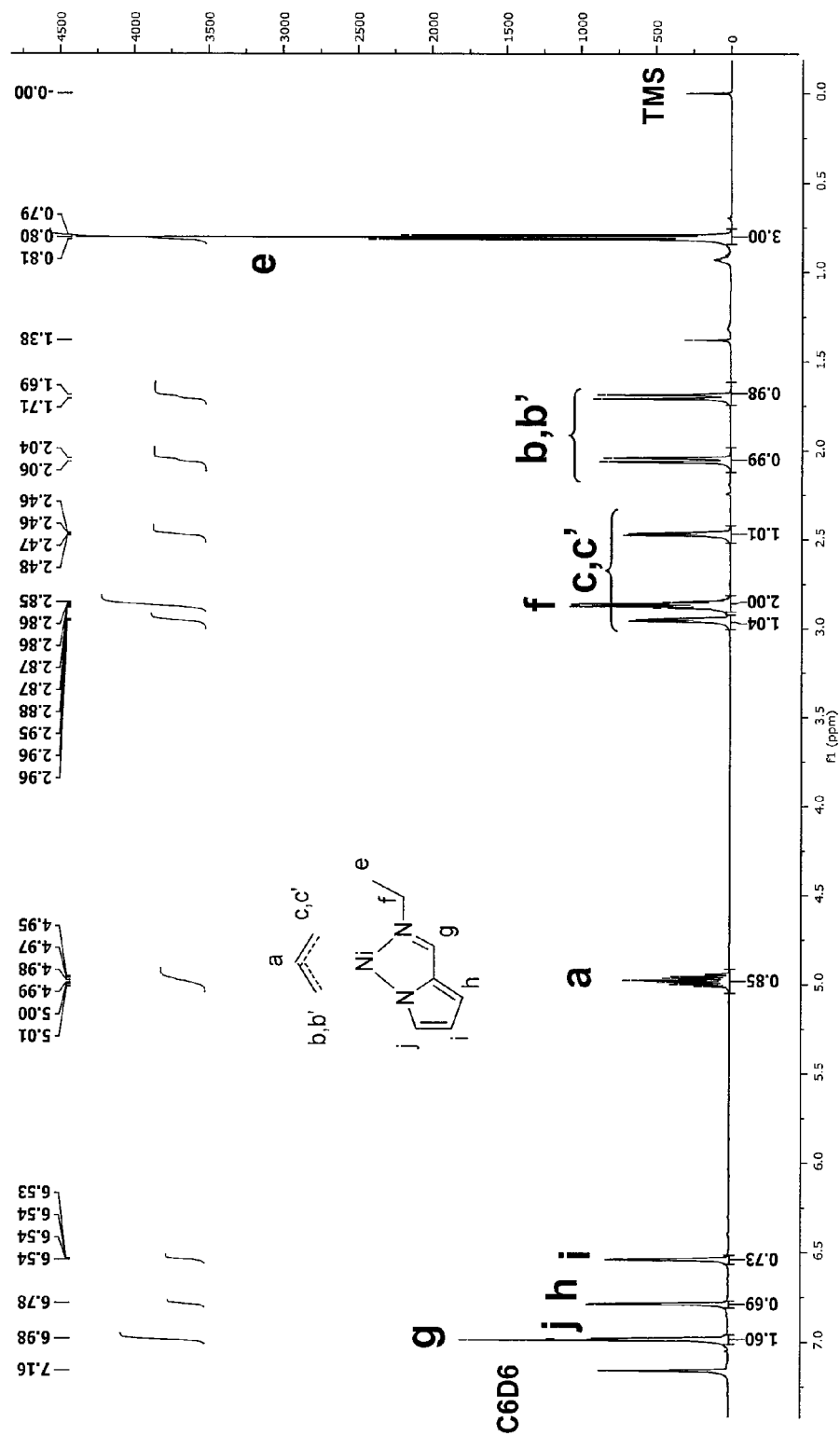
FIG 3 NMR 1H of allyl 2-ethyliminemethylpyrrolyl nickel(II) in C6D6

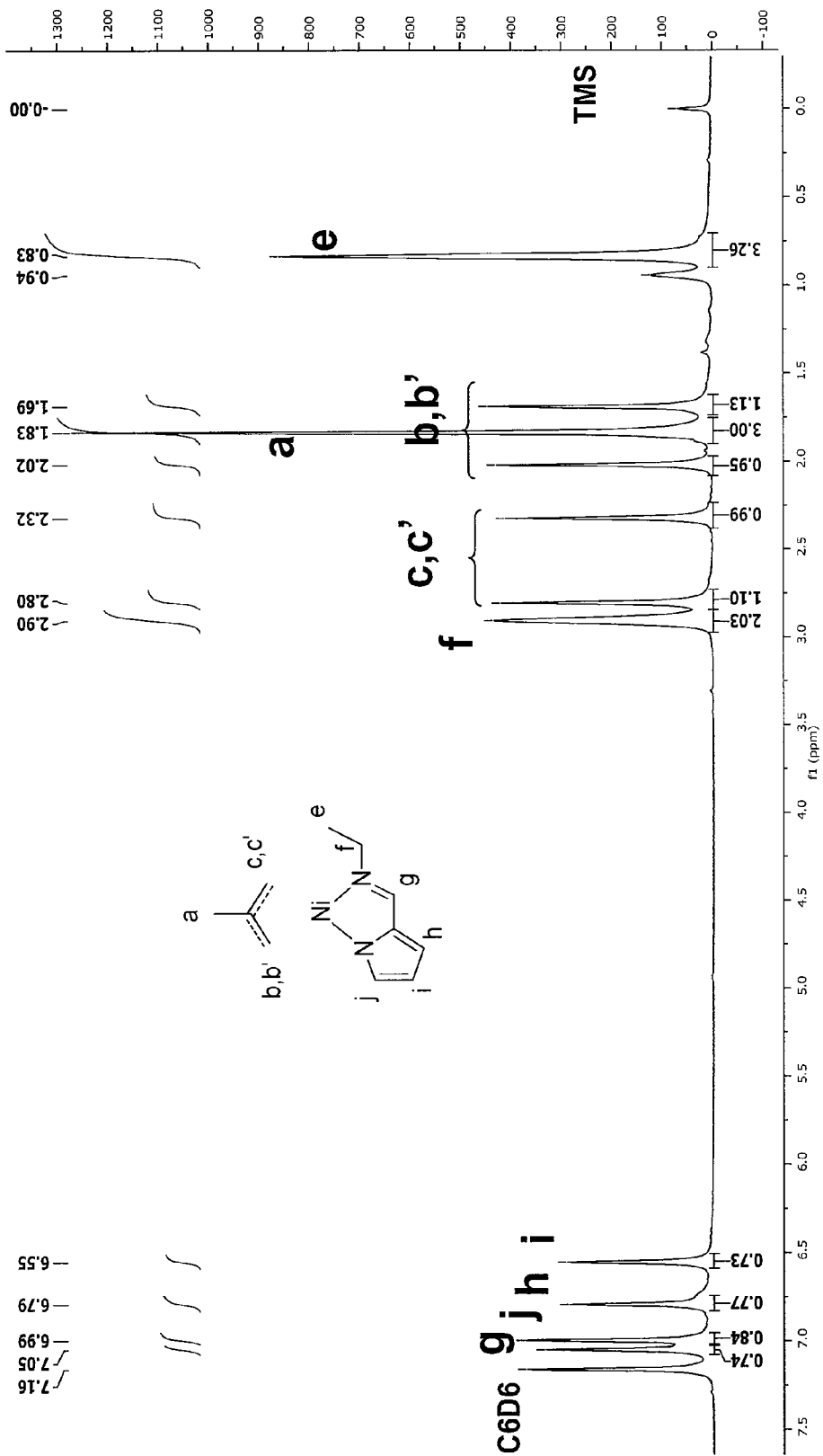
FIG 4: NMR 1H of 2-methylallyl 2-ethyliminemethylpyrrolyl nickel(II) in C$_6$D$_6$

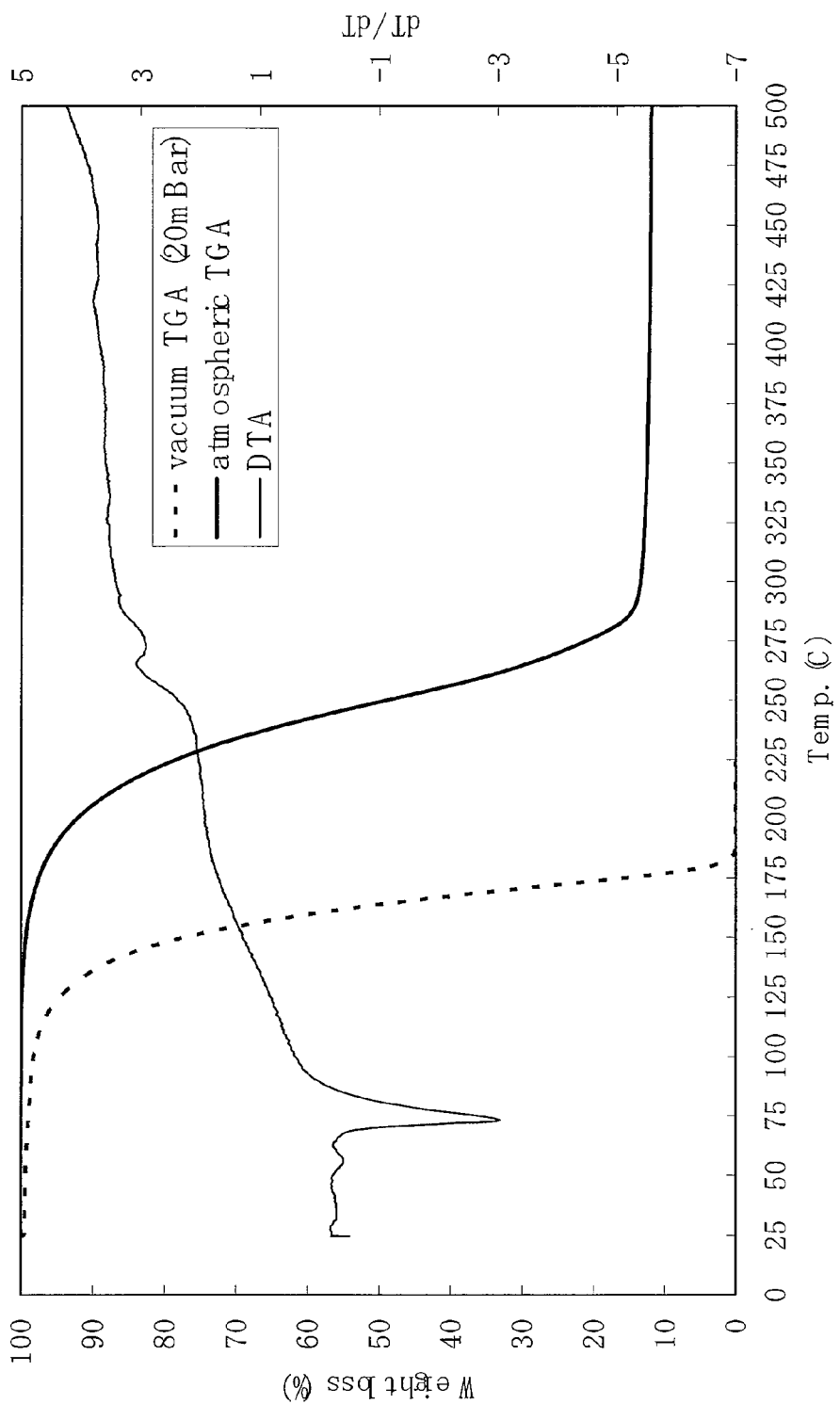
FIG 5 Atmospheric and vacuum TGA of allyl 2-isopropyliminemethylpyrrolyl nickel(II).

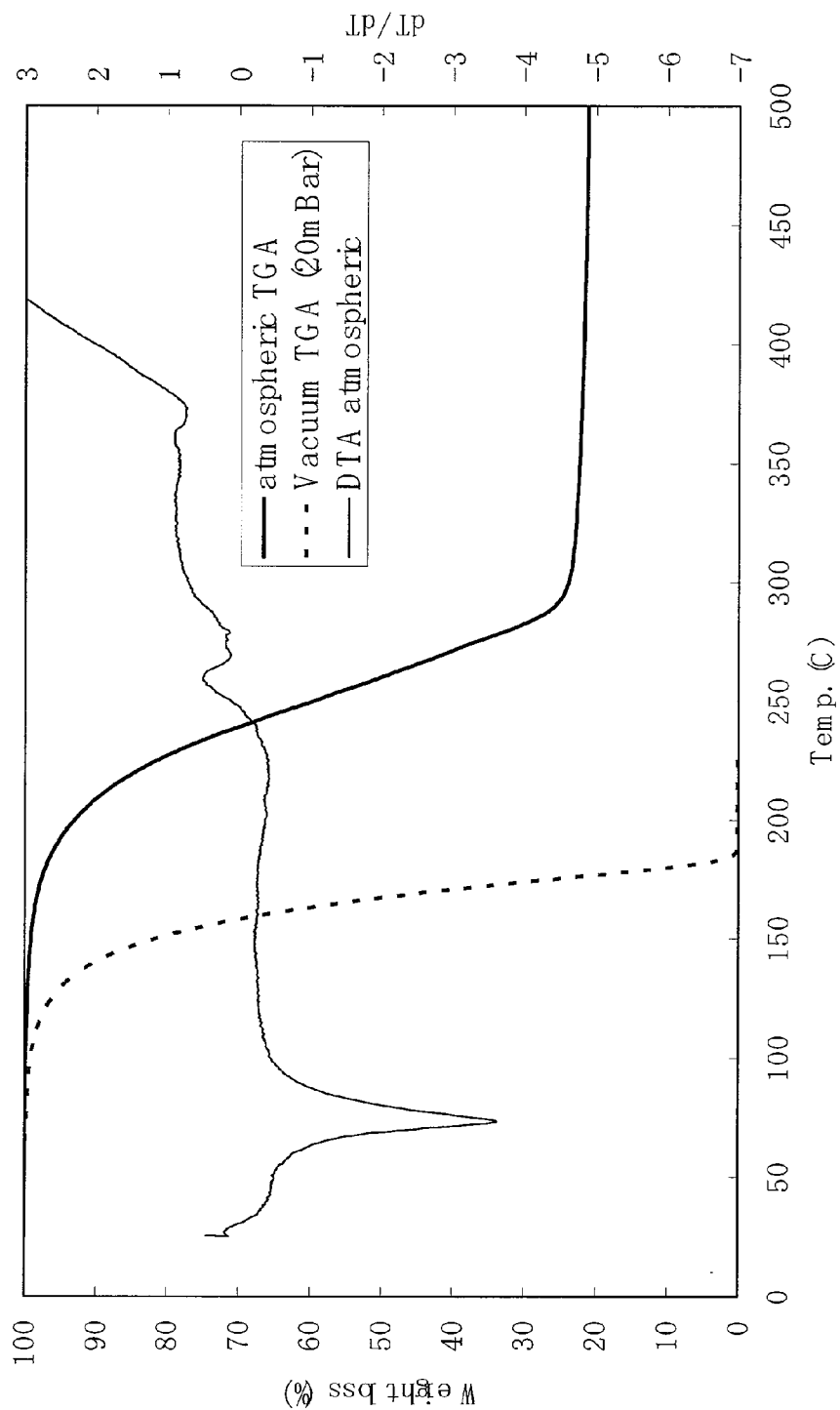
FIG 6 Atmospheric and vacuum TGA of 1-methylallyl 2-isopropyliminemethylpyrrolyl nickel(II).

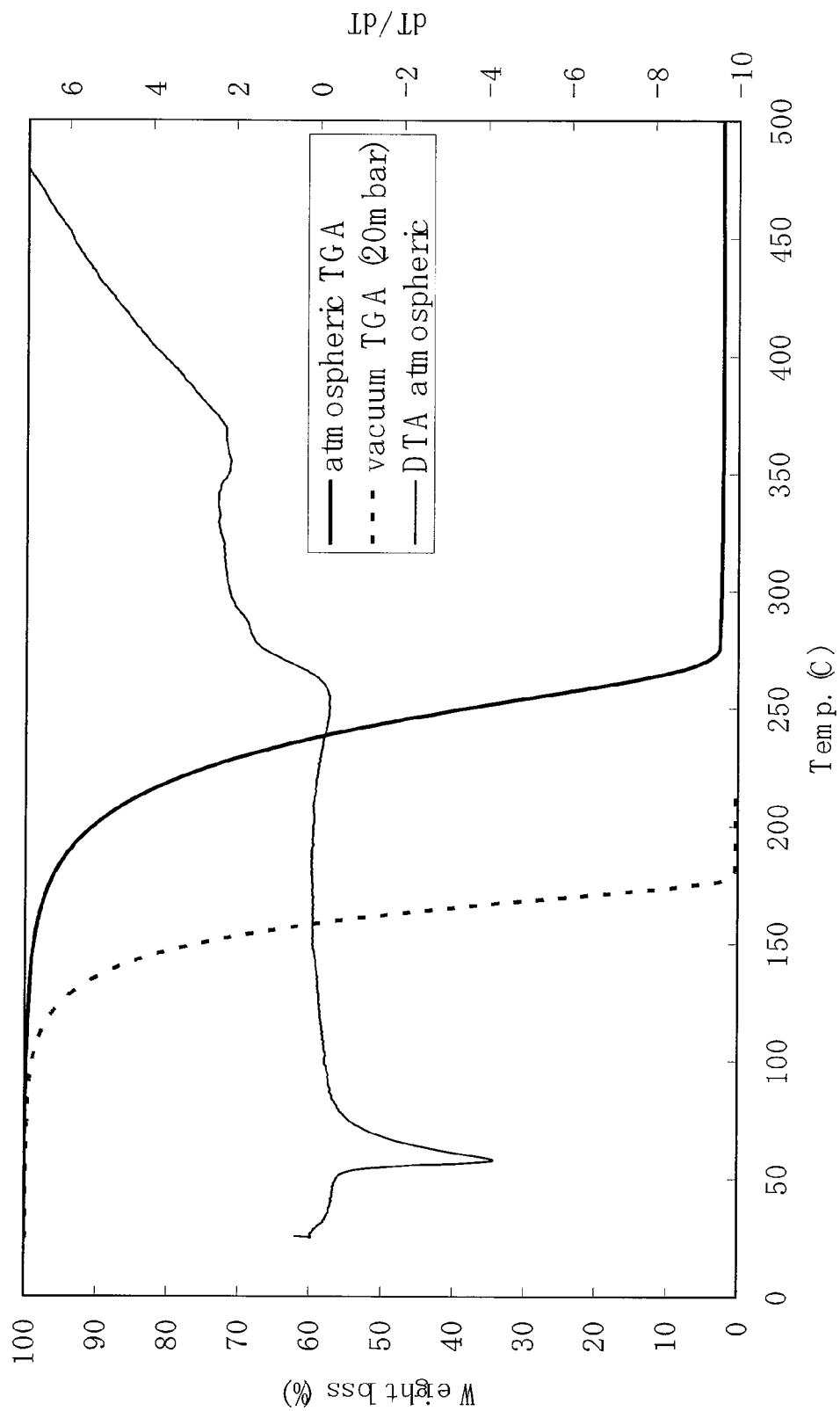
FIG 7 Atmospheric and vacuum TGA of 2-methylallyl 2-isopropyliminemethylpyrrolyl nickel(II).

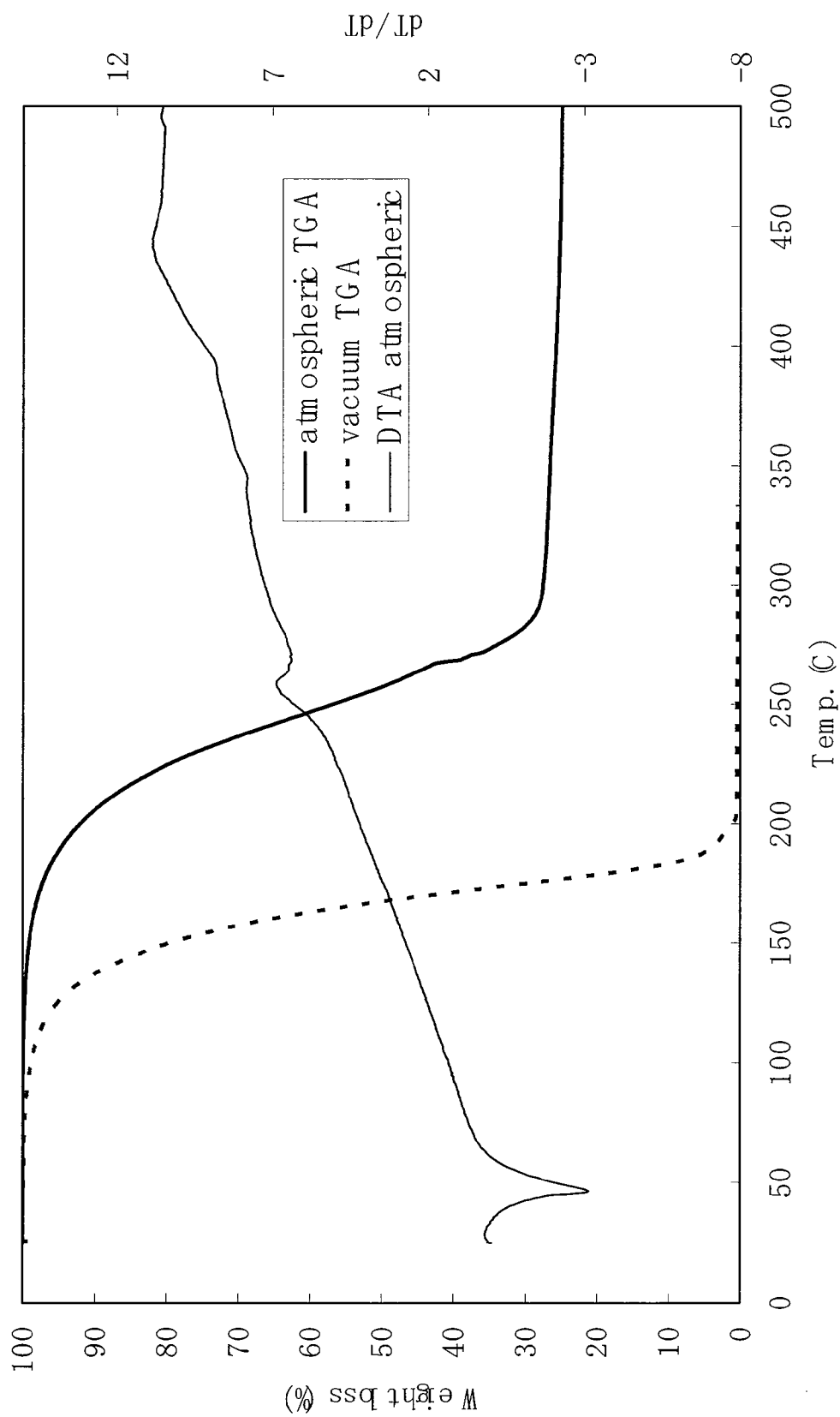
FIG 8 Atmospheric and vacuum TGA of allyl 2-ethyliminemethylpyrrolyl nickel(II).

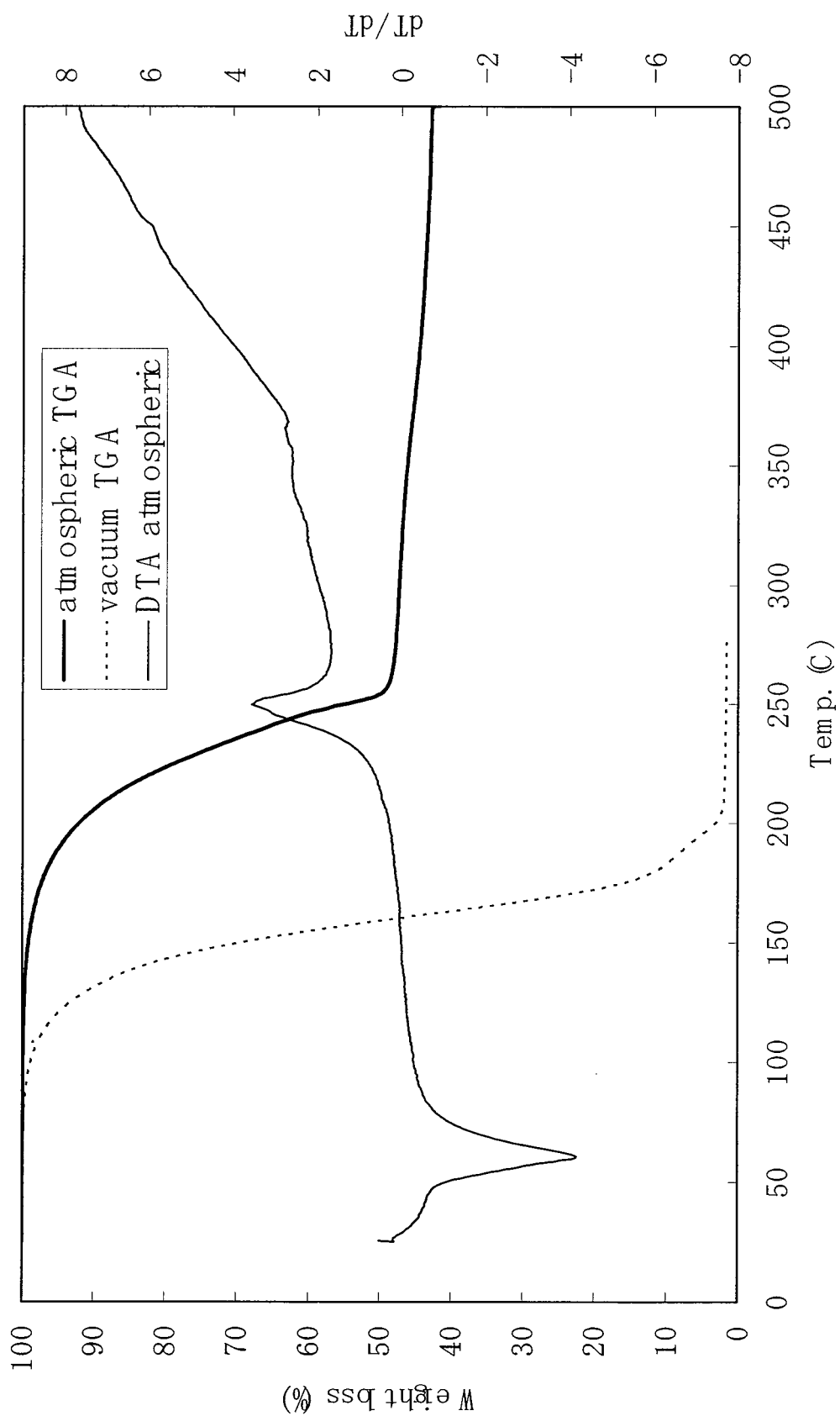
FIG 9 Atmospheric and vacuum TGA of 2-methylallyl 2-ethyliminemethylpyrrolyl nickel(II).

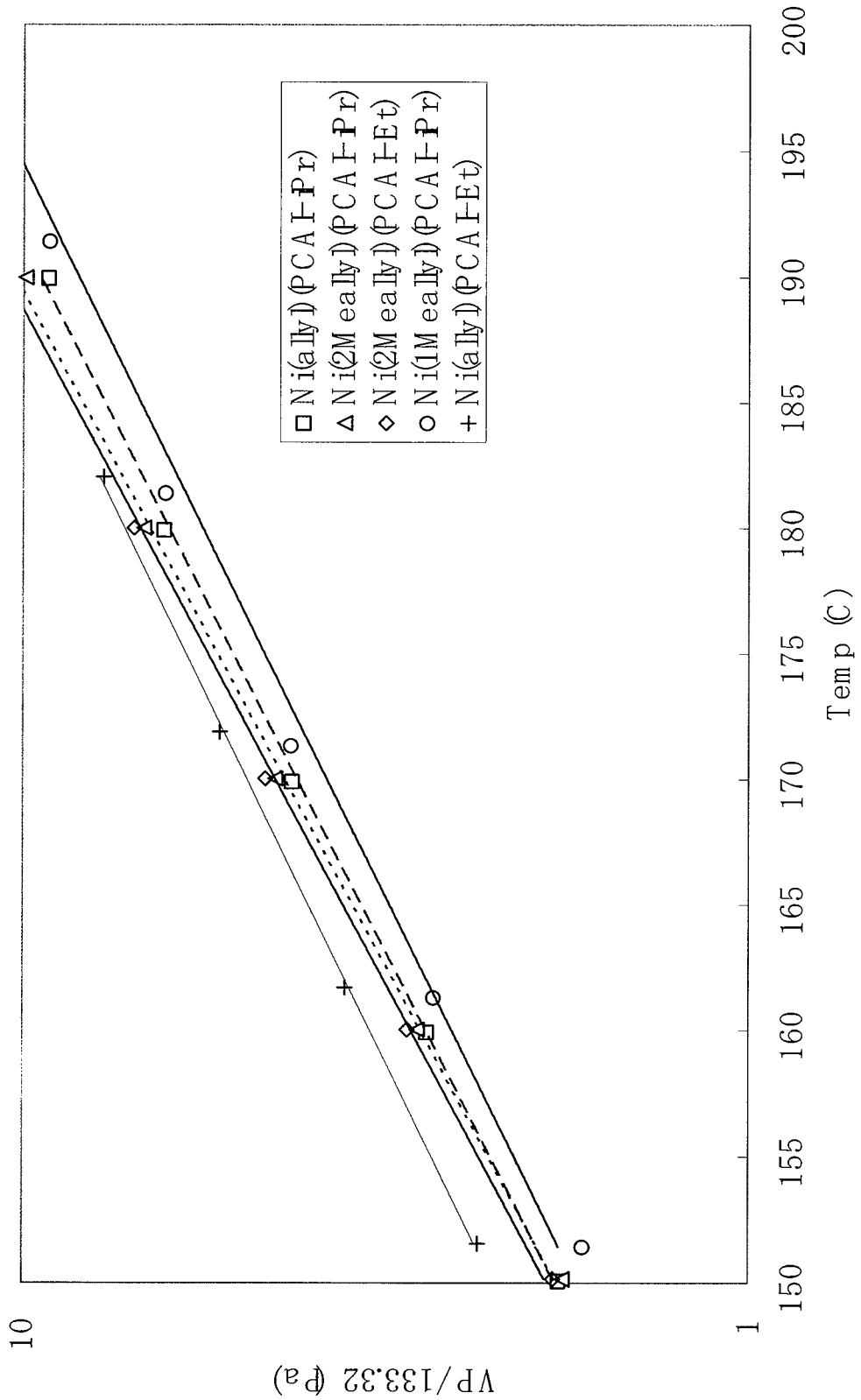
FIG 10 Vapor pressure of allyl pyrroles-2-methylaldiminate nickel(II) precursors.

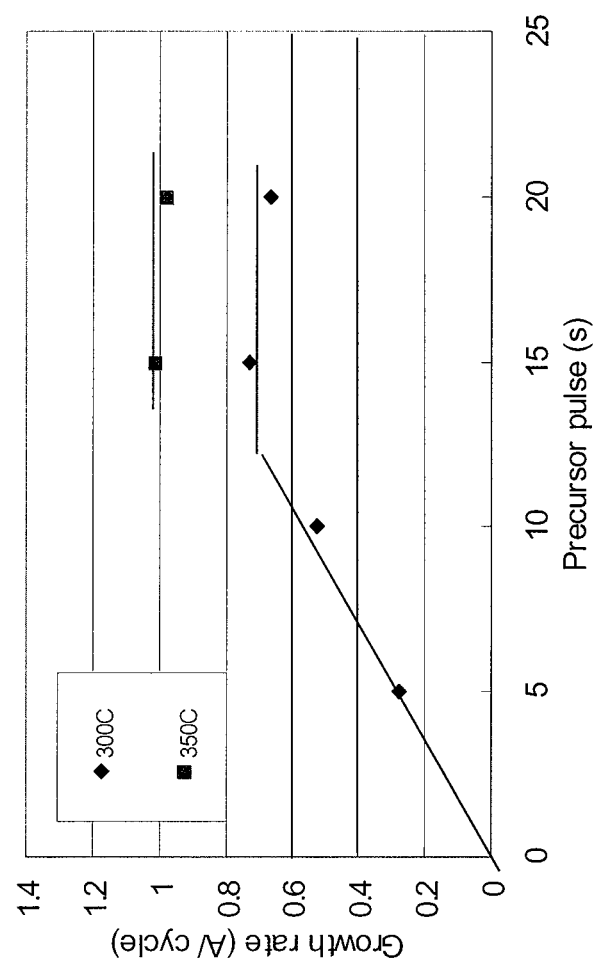
FIG 11 PEALD saturation using allyl pyrroles-2-methylaldiminate nickel(II).

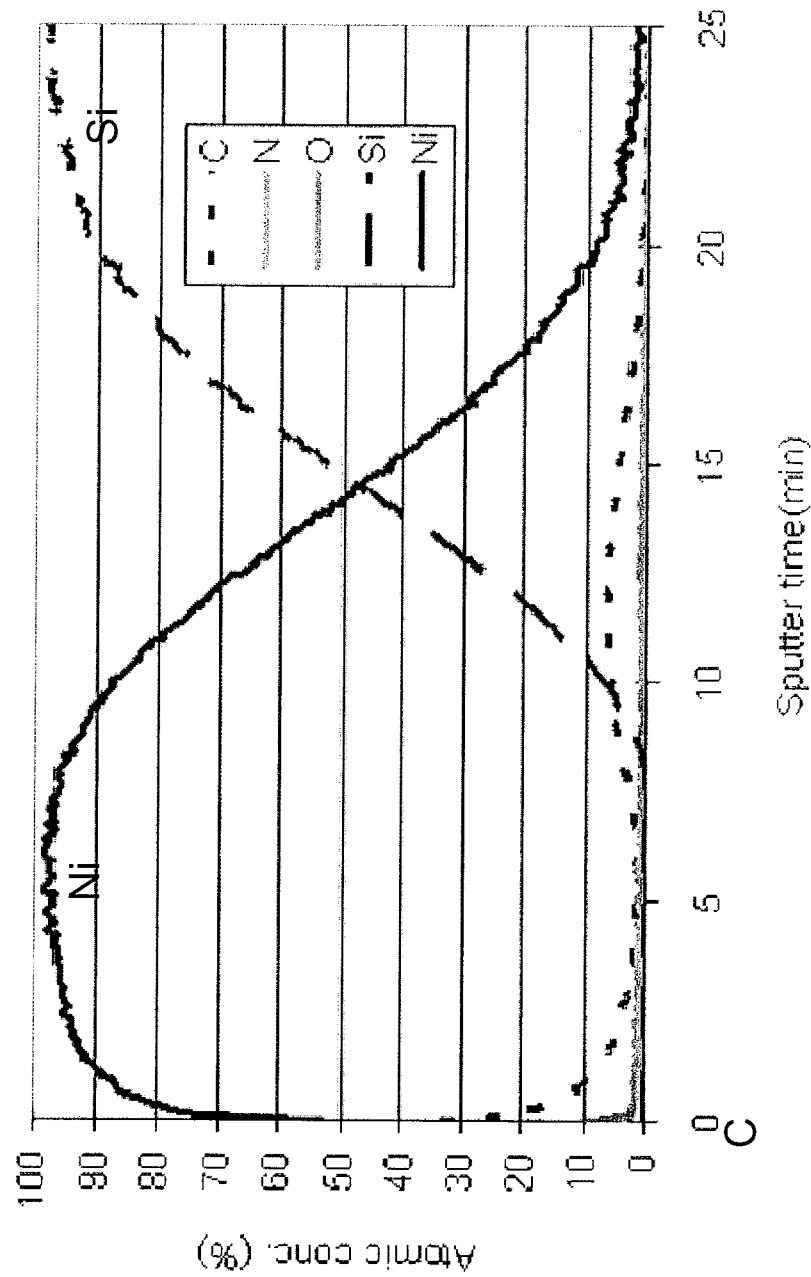
FIG 12 AES of a nickel films grown in PEALD mode at 400°C using allyl pyrroles-2-methylaldiminate nickel(II).

HETEROLEPTIC (ALLYL)(PYRROLES-2-ALDIMINATE) METAL-CONTAINING PRECURSORS, THEIR SYNTHESIS AND VAPOR DEPOSITION THEREOF TO DEPOSIT METAL-CONTAINING FILMS

CROSS-REFERENCE TO RELATED APPLICATIONS

This application is a 371 of International PCT Application PCT/US2012/044950, filed Jun. 29, 2012, which claims priority to U.S. provisional application No. 61/510,857, filed Jul. 22, 2011, the entire contents of each of which are incorporated herein by reference.

TECHNICAL FIELD

Disclosed are metal-containing precursors having the formula

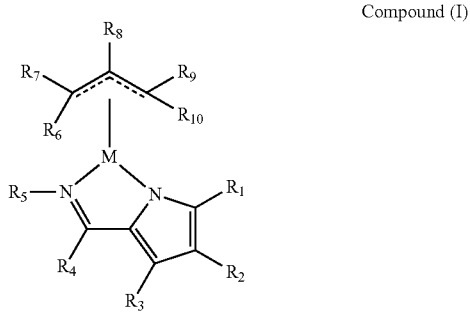

Compound (I)

wherein:
M is a metal selected from Ni, Co, Mn, Pd; and
each of $R_1$, $R_2$, $R_3$, $R_4$, $R_5$, $R_6$, $R_7$, $R_8$, $R_9$, and $R_{10}$ are independently selected from H; a C1-C4 linear, branched, or cyclic alkyl group; a C1-C4 linear, branched, or cyclic alkylsilyl group (mono, bis, or tris alkyl); a C1-C4 linear, branched, or cyclic alkylamino group; or a C1-C4 linear, branched, or cyclic fluoroalkyl group.

Also disclosed are methods of synthesizing and using the disclosed metal-containing precursors to deposit metal-containing films on a substrate via a vapor deposition process.

BACKGROUND

During the fabrication of a transistor, silicide layers may be used to improve the conductivity of polysilicon. For instance nickel and cobalt silicide ($CoSi_2$, NiSi) may be used as a contact in the source and drain of the transistor to improve conductivity. The process to form metal silicide begins by the deposition of a thin transition metal layer, nickel for instance, on the polysilicon. The metal and a portion of the polysilicon are then alloyed together to form the metal silicide layer.

Chemical Vapor Deposition (CVD) and Atomic Layer Deposition (ALD) are the main gas phase chemical process used to control deposition at the atomic scale and create extremely thin coatings. In a typical CVD process, the wafer is exposed to one or more volatile precursors, which react and/or decompose on the substrate surface to produce the desired deposit. ALD process are based on sequential and saturating surface reactions of alternatively applied metal precursor, separated by inert gas purging.

In order to get high-purity, thin, high-performance solid materials on the wafer, the metal-containing precursors are required to have high purity, high thermal stability, and high volatility. Furthermore they should vaporize rapidly and at a reproducible rate, conditions that are usually met by liquid precursors, but not by solid precursors (See R. G. Gordon et Al. FutureFab International, 2005, 18, 126-128).

Available metal precursors (nickel, cobalt, manganese, palladium) suffer either from poor volatility or low thermal stability which results in carbon incorporation in the films during the deposition process. Several Ni precursors such as a glyoximato (M. Becht, et al., J. Phys. IV (1995) C5-465), β-diketonato (T. Maruyama, T. Tago, J. Mater. Sci. 28 (1993) 5345), or cyclopentadienyl nickel (L. Brissonneau, C. Vahlas, Chem. Vap. Deposit. 5 (1999) 135, 143; J.-K. Kang, S.-W. Rhee, J. Mater. Res. 15 (2000) 1828) were used for deposition process. All are solids below 150° C., and their volatilities are very low. High deposition temperatures were needed to obtain nickel films with those precursors. High deposition temperature causes the decomposition of organic ligands resulting in the increase of residual carbon, which often increases electrical resistivity in the deposited Ni film.

Amidinate transition metal precursors are now well described in the literature (See R. G. Gordon et Al. Inorg. Chem. 2003, 42, 7951-7958; R. G. Gordon Chem. Mater. 2010 22, 3060-3066). They have been used for deposition of Ni by CVD. Although volatile, those precursors are usually solids with high melting point (>70° C.) and can suffer from thermal instability (nickel for instance), which is a drawback for the ALD process. On the other hand, bis-cyclopentadienyl precursors are known to be liquid or low melting point solid, and still volatile depending on the substitution on the cyclopentadienyl. For instance, $Ni(Me-Cp)_2$: solid mp=34-36° C., $Ni(Et-Cp)_2$: liquid, $Ni(iPr-Cp)_2$: liquid. However bis-cyclopentadienyl precursors still suffer from thermal stability, with nickel for instance. Alternatively Ni(allyl)(cyclopentadienyl) precursor was used for the deposition of nickel film. However films contain high content of carbon. (T. Kada, Journal of Crystal Growth 275 (2005) e1115-e1119).

Heteroleptic metal precursors containing allyl ligands are relatively scarce in the literature. Nickel and palladium allyl-diketiminate can be prepared according to J. Organomet. Chem. 2009, 694, 667. The compounds are obtained by reaction of the lithium salt of the diketimine with nickel or palladium-allyl-chloride dimer at low temperature. Substituents on the diketiminate are however aromatic, which is not convenient for ALD/CVD application because of resulting low volatility. Nickel(allyl)(pyrroles-2-aldiminate) precursors can also be prepared according to Dalton Trans., 2003, 4431-4436; J. Organomet. Chem. 693 (2008) 3902-3906); WO9830609 (A1). Precursors are also prepared by reacting the lithium salt of pyrroles-2-aldiminate with nickel-allyl-chloride dimer.

As a consequence, a need remains for new transition metal-containing precursors suitable for CVD or ALD process. Desirable properties of the metal-containing precursors for these applications are: i) liquid form or low melting point solid; ii) high volatility; iii) sufficient thermal stability to avoid decomposition during handling and delivery; and iv) appropriate reactivity during CVD/ALD process.

SUMMARY

Disclosed are metal-containing precursors having the formula:

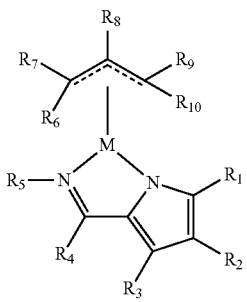

Compound (I)

wherein
M is a metal selected from the group consisting of Ni, Co, Mn, and Pd; and
each of $R_1$, $R_2$, $R_3$, $R_4$, $R_5$, $R_6$, $R_7$, $R_8$, $R_9$, and $R_{10}$ are independently selected from H; a C1-C4 linear, branched, or cyclic alkyl group; a C1-C4 linear, branched, or cyclic alkylsilyl group (mono, bis, or tris alkyl); a C1-C4 linear, branched, or cyclic alkylamino group; or a C1-C4 linear, branched, or cyclic fluoroalkyl group.

The disclosed precursors may be selected from:
(allyl)(2-iminemethylpyrrolyl) nickel(II);
(allyl)(2-methyliminemethylpyrrolyl) nickel (II);
(allyl)(2-ethyliminemethylpyrrolyl) nickel (II);
(allyl)(2-isopropyliminemethylpyrrolyl) nickel(II);
(allyl)(2-npropyliminemethylpyrrolyl) nickel (II);
(allyl)(2-nbutyliminemethylpyrrolyl) nickel (II);
(allyl)(2-secbutyliminemethylpyrrolyl) nickel (II);
(allyl)(2-isobutyliminemethylpyrrolyl) nickel (II);
(allyl)(2-tertbutyliminemethylpyrrolyl) nickel (II);
(allyl)(2-trimethylsilylbutyliminemethylpyrrolyl) nickel (II);
(1-Methylallyl)(2-iminemethylpyrrolyl) nickel(II);
(1-Methylallyl)(2-methyliminemethylpyrrolyl) nickel (II);
(1-Methylallyl)(2-ethyliminemethylpyrrolyl) nickel (II);
(1-Methylallyl)(2-isopropyliminemethylpyrrolyl) nickel(II);
(1-Methylallyl)(2-npropyliminemethylpyrrolyl) nickel (II);
(1-Methylallyl)(2-nbutyliminemethylpyrrolyl) nickel (II);
(1-Methylallyl)(2-secbutyliminemethylpyrrolyl) nickel (II);
(1-Methylallyl)(2-isobutyliminemethylpyrrolyl) nickel (II);
(1-Methylallyl)(2-tertbutyliminemethylpyrrolyl) nickel (II);
(1-Methylallyl)(2-trimethylsilylbutyliminemethylpyrrolyl) nickel (II);
(2-Methylallyl)(2-iminemethylpyrrolyl) nickel(II);
(2-Methylallyl)(2-methyliminemethylpyrrolyl) nickel (II);
(2-Methylallyl)(2-ethyliminemethylpyrrolyl) nickel (II);
(2-Methylallyl)(2-isopropyliminemethylpyrrolyl) nickel(II);
(2-Methylallyl)(2-npropyliminemethylpyrrolyl) nickel (II);
(2-Methylallyl)(2-nbutyliminemethylpyrrolyl) nickel (II);
(2-Methylallyl)(2-secbutyliminemethylpyrrolyl) nickel (II);
(2-Methylallyl)(2-isobutyliminemethylpyrrolyl) nickel (II);
(2-Methylallyl)(2-tertbutyliminemethylpyrrolyl) nickel (II);
(2-Methylallyl)(2-trimethylsilylbutyliminemethylpyrrolyl) nickel (II);
(allyl)(2-iminemethylpyrrolyl) cobalt(II);
(allyl)(2-methyliminemethylpyrrolyl) cobalt (II);
(allyl)(2-ethyliminemethylpyrrolyl) cobalt (II);
(allyl)(2-isopropyliminemethylpyrrolyl) cobalt (II);
(allyl)(2-npropyliminemethylpyrrolyl) cobalt (II);
(allyl)(2-nbutyliminemethylpyrrolyl) cobalt (II);
(allyl)(2-secbutyliminemethylpyrrolyl) cobalt (II);
(allyl)(2-isobutyliminemethylpyrrolyl) cobalt (II);
(allyl)(2-tertbutyliminemethylpyrrolyl) cobalt (II);
(allyl)(2-trimethylsilylbutyliminemethylpyrrolyl) cobalt (II);
(1-Methylallyl)(2-iminemethylpyrrolyl) cobalt (II);
(1-Methylallyl)(2-methyliminemethylpyrrolyl) cobalt (II);
(1-Methylallyl)(2-ethyliminemethylpyrrolyl) cobalt (II);
(1-Methylallyl)(2-isopropyliminemethylpyrrolyl) cobalt (II);
(1-Methylallyl)(2-npropylinninemethylpyrrolyl) cobalt (II);
(1-Methylallyl)(2-nbutyliminemethylpyrrolyl) cobalt (II);
(1-Methylallyl)(2-secbutyliminemethylpyrrolyl) cobalt (II);
(1-Methylallyl)(2-isobutyliminemethylpyrrolyl) cobalt (II);
(1-Methylallyl)(2-tertbutyliminemethylpyrrolyl) cobalt (II);
(1-Methylallyl)(2-trimethylsilylbutyliminemethylpyrrolyl) cobalt (II);
(2-Methylallyl)(2-iminemethylpyrrolyl) cobalt (II);
(2-Methylallyl)(2-methyliminemethylpyrrolyl) cobalt (II);
(2-Methylallyl)(2-ethyliminemethylpyrrolyl) cobalt (II);
(2-Methylallyl)(2-isopropyliminemethylpyrrolyl) cobalt (II);
(2-Methylallyl)(2-npropyliminemethylpyrrolyl) cobalt (II);
(2-Methylallyl)(2-nbutyliminemethylpyrrolyl) cobalt (II);
(2-Methylallyl)(2-secbutyliminemethylpyrrolyl) cobalt (II);
(2-Methylallyl)(2-isobutyliminemethylpyrrolyl) cobalt (II);
(2-Methylallyl)(2-tertbutyliminemethylpyrrolyl) cobalt (II);
(2-Methylallyl)(2-trimethylsilylbutyliminemethylpyrrolyl) cobalt (II);
(allyl)(2-iminemethylpyrrolyl) manganese(II);
(allyl)(2-methyliminemethylpyrrolyl) manganese (II);
(allyl)(2-ethyliminemethylpyrrolyl) manganese (II);
(allyl)(2-isopropyliminemethylpyrrolyl) manganese (II);
(allyl)(2-npropyliminemethylpyrrolyl) manganese (II);
(allyl)(2-nbutyliminemethylpyrrolyl) manganese (II);
(allyl)(2-secbutyliminemethylpyrrolyl) manganese (II);
(allyl)(2-isobutyliminemethylpyrrolyl) manganese (II);
(allyl)(2-tertbutyliminemethylpyrrolyl) manganese (II);
(allyl)(2-trimethylsilylbutyliminemethylpyrrolyl) manganese (II);
(1-Methylallyl)(2-iminemethylpyrrolyl) manganese (II);
(1-Methylallyl)(2-methyliminemethylpyrrolyl) manganese (II);
(1-Methylallyl)(2-ethyliminemethylpyrrolyl) manganese (II);
(1-Methylallyl)(2-isopropyliminemethylpyrrolyl) manganese (II);
(1-Methylallyl)(2-npropyliminemethylpyrrolyl) manganese (II);
(1-Methylallyl)(2-nbutyliminemethylpyrrolyl) manganese (II);
(1-Methylallyl)(2-secbutyliminemethylpyrrolyl) manganese (II);
(1-Methylallyl)(2-isobutyliminemethylpyrrolyl) manganese (II);
(1-Methylallyl)(2-tertbutyliminemethylpyrrolyl) manganese (II);
(1-Methylallyl)(2-trimethylsilylbutyliminemethylpyrrolyl) manganese (II);
(2-Methylallyl)(2-iminemethylpyrrolyl) manganese (II);
(2-Methylallyl)(2-methyliminemethylpyrrolyl) manganese (II);
(2-Methylallyl)(2-ethyliminemethylpyrrolyl) manganese (II);

(2-Methylallyl)(2-isopropyliminemethylpyrrolyl) manganese (II);
(2-Methylallyl)(2-npropyliminemethylpyrrolyl) manganese (II);
(2-Methylallyl)(2-nbutyliminemethylpyrrolyl) manganese (II);
(2-Methylallyl)(2-secbutyliminemethylpyrrolyl) manganese (II);
(2-Methylallyl)(2-isobutyliminemethylpyrrolyl) manganese (II);
(2-Methylallyl)(2-tertbutyliminemethylpyrrolyl) manganese (II);
(2-Methylallyl)(2-trimethylsilylbutyliminemethylpyrrolyl) manganese (II);
(allyl)(2-iminemethylpyrrolyl) palladium(II);
(allyl)(2-methyliminemethylpyrrolyl) palladium (II);
(allyl)(2-ethyliminemethylpyrrolyl) palladium (II);
(allyl)(2-isopropyliminemethylpyrrolyl) palladium (II);
(allyl)(2-npropyliminemethylpyrrolyl) palladium (II);
(allyl)(2-nbutyliminemethylpyrrolyl) palladium (II);
(allyl)(2-secbutyliminemethylpyrrolyl) palladium (II);
(allyl)(2-isobutyliminemethylpyrrolyl) palladium (II);
(allyl)(2-tertbutyliminemethylpyrrolyl) palladium (II);
(allyl)(2-trimethylsilylbutyliminemethylpyrrolyl) palladium (II);
(1-Methylallyl)(2-iminemethylpyrrolyl) palladium (II);
(1-Methylallyl)(2-methyliminemethylpyrrolyl) palladium (II);
(1-Methylallyl)(2-ethyliminemethylpyrrolyl) palladium (II);
(1-Methylallyl)(2-isopropyliminemethylpyrrolyl) palladium (II);
(1-Methylallyl)(2-npropyliminemethylpyrrolyl) palladium (II);
(1-Methylallyl)(2-nbutyliminemethylpyrrolyl) palladium (II);
(1-Methylallyl)(2-secbutyliminemethylpyrrolyl) palladium (II);
(1-Methylallyl)(2-isobutyliminemethylpyrrolyl) palladium (II);
(1-Methylallyl)(2-tertbutyliminemethylpyrrolyl) palladium (II);
(1-Methylallyl)(2-trimethylsilylbutyliminemethylpyrrolyl) palladium (II);
(2-Methylallyl)(2-iminemethylpyrrolyl) palladium (II);
(2-Methylallyl)(2-methyliminemethylpyrrolyl) palladium (II);
(2-Methylallyl)(2-ethyliminemethylpyrrolyl) palladium (II);
(2-Methylallyl)(2-isopropyliminemethylpyrrolyl) palladium (II);
(2-Methylallyl)(2-npropyliminemethylpyrrolyl) palladium (II);
(2-Methylallyl)(2-nbutyliminemethylpyrrolyl) palladium (II);
(2-Methylallyl)(2-secbutyliminemethylpyrrolyl) palladium (II);
(2-Methylallyl)(2-isobutyliminemethylpyrrolyl) palladium (II);
(2-Methylallyl)(2-tertbutyliminemethylpyrrolyl) palladium (II); or
(2-Methylallyl)(2-trimethylsilylbutyliminemethylpyrrolyl) palladium (II).

Preferably, the metal-containing precursor is (2-methylallyl)(2-isopropyliminemethylpyrrolyl) nickel(II) or (allyl)(2-isopropyliminemethylpyrrolyl) nickel(II).

Also disclosed are processes for the deposition of a metal-containing film on a substrate. One or more of the disclosed metal-containing precursors above are introduced into a reactor having at least one substrate disposed therein. At least part of the metal-containing precursor is deposited onto the at least one substrate to form a metal-containing film. The disclosed methods may further include one or more of the following aspects:
 introducing at least one reactant into the reactor;
 the reactant being selected from the group consisting of $H_2$, $NH_3$, $SiH_4$, $Si_2H_6$, $Si_3H_8$, $SiH_2Me_2$, $SiH_2Et_2$, $N(SiH_3)_3$, hydrogen radicals thereof; and mixtures thereof;
 the reactant being selected from the group consisting of: $O_2$, $O_3$, $H_2O$, NO, $N_2O$, oxygen radicals thereof; and mixtures thereof;
 the metal-containing precursor and the reactant being introduced into the reactor substantially simultaneously and the reactor is configured for chemical vapor deposition;
 the reactor being configured for plasma enhanced chemical vapor deposition;
 the metal-containing precursor and the reactant being introduced into the chamber sequentially and the reactor is configured for atomic layer deposition; and
 the reactor being configured for plasma enhanced atomic layer deposition.

Notation and Nomenclature

Certain abbreviations, symbols, and terms are used throughout the following description and claims, and include: the term "alkyl group" refers to saturated functional groups containing exclusively carbon and hydrogen atoms. Further, the term "alkyl group" refers to linear, branched, or cyclic alkyl groups. Examples of linear alkyl groups include without limitation, methyl groups, ethyl groups, propyl groups, butyl groups, etc. Examples of branched alkyls groups include without limitation, t-butyl. Examples of cyclic alkyl groups include without limitation, cyclopropyl groups, cyclopentyl groups, cyclohexyl groups, etc.

As used herein, the abbreviation, "Me," refers to a methyl group; the abbreviation, "Et," refers to an ethyl group; the abbreviation, "Pr," refers to a propyl group; the abbreviation, "iPr," refers to an isopropyl group; the abbreviation "Bu" refers to butyl; the abbreviation "tBu" refers to tert-butyl; the abbreviation "sBu" refers to sec-butyl; the abbreviation "acac" refers to acetylacetonato/acetylacetonate (acetylacetonato being the ligand and acetylacetonate being a molecule), with acetylacetonate being illustrated below; the abbreviation "tmhd" refers to 2,2,6,6-tetramethyl-3,5-heptadionato; the abbreviation "od" refers to 2,4-octadionato; the abbreviation "mhd" refers to 2-methyl-3,5-hexadinonato; the abbreviation "tmod" refers to 2,2,6,6-tetramethyl-3,5-octanedionato; the abbreviation "ibpm" refers to 2,2,6-trimethyl-3-5-heptadionato; the abbreviation "hfac" refers to hexafluoroacetylacetonato; the abbreviation "tfac" refers to trifluoroacetylacetonato; the abbreviation "Cp" refers to cyclopentadienyl; the abbreviation "Cp*" refers to pentamethylcyclopentadienyl; the abbreviation "op" refers to (open) pentadienyl; the abbreviation "cod" refers to cyclooctadiene; the abbreviation "dkti" refers to diketiminate/diketimine (ligand/molecule), with diketiminate illustrated below (with $R^1$ being the R ligand connected to the C at the apex of the dkti ligand in the structure below, each $R^2$ independently being the R ligand connected to the C in the dkti chain, and each $R^3$ independently being the R ligand connected to the N; for example $HC(C(Me)N(Me))_2$); the abbreviation "emk" refers to enaminoketonate/enaminoketone (ligand/molecule), with enaminoketonate illustrated below (where each R is independently selected from H and a C1-C6 linear, branched, or cyclic alkyl or aryl group) (emk is also sometimes referred to as ketoiminate/ketoimine); the abbreviation "amd" refers to amidinate, illustrated below (with $R^1$ being the R ligand connected to C in the structure below and each $R^2$ independently being the R ligand connected to each N; for example MeC(N (SiMe$_3$)$_2$); the abbreviation "formd" refers to formamidinate, illustrated below; the abbreviation "dab" refers to diazabutadiene, illustrated below (where each R is independently selected from H and a C1-C6 linear, branched, or cyclic alkyl or aryl group).

For a better understanding, the generic structures of some of these ligands are represented below. These generic structures may be further substituted by substitution groups, wherein each R is independently selected from: H; a C1-C6 linear, branched, or cyclic alkyl or aryl group; an amino substituent such as $NR_1R_2$ or $NR_1R_2R_3$, with $MNR_1R_2R_3$ illustrated below, where each $R_1$, $R_2$ and $R_3$ is independently selected from H and a C1-C6 linear, branched, or cyclic alkyl or aryl group; and an alkoxy substituent such as OR, or $OR_4R_5$, with $MOR_4R_5$ illustrated below, where each R, $R_4$ and $R_5$ is independently selected from H and a C1-C6 linear, branched, or cyclic alkyl or aryl group.

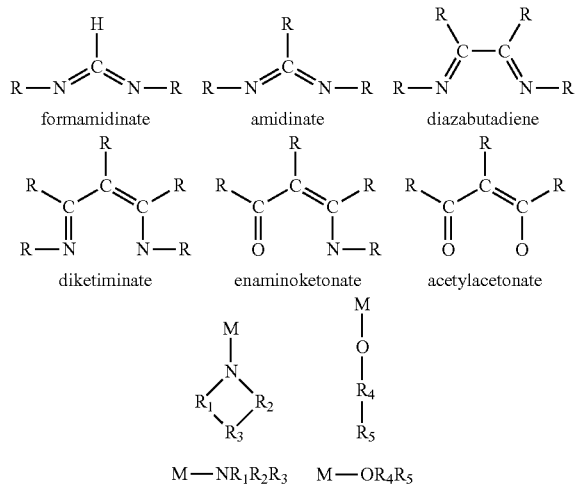

BRIEF DESCRIPTION OF THE FIGURES

For a further understanding of the nature and objects of the present invention, reference should be made to the following detailed description, taken in conjunction with the accompanying figure wherein:

FIG. 1 is a NMR spectrum of allyl 2-isopropyliminemethylpyrrolylnickel(II);

FIG. 2 is a NMR spectrum of 2-methylallyl 2-isopropylimine methylpyrrolyl nickel(II);

FIG. 3 is a NMR spectrum of allyl 2-ethylimine methylpyrrolyl nickel(II);

FIG. 4 is a NMR spectrum of 2-methylallyl 2-ethylimine methylpyrrolyl nickel(II);

FIG. 5 is an atmospheric and vacuum thermogravimetric analysis (TGA) graph of allyl 2-isopropyliminemethylpyrrolylnickel(II);

FIG. 6 is an atmospheric and vacuum TGA graph of 1-methylallyl 2-isopropyliminemethylpyrrolyl nickel(II);

FIG. 7 is an atmospheric and vacuum TGA graph of 2-methylallyl 2-isopropyliminemethylpyrrolyl nickel(II);

FIG. 8 is an atmospheric and vacuum TGA graph of allyl 2-ethylimine methyl pyrrolyl nickel(II);

FIG. 9 is an atmospheric and vacuum TGA of 2-methylallyl 2-ethylimine methyl pyrrolyl nickel(II);

FIG. 10 is a graph of the vapor pressures of multiple allyl pyrroles-2-methylaldiminate nickel(II) precursors;

FIG. 11 is a graph of the plasma enhanced atomic layer deposition saturation curve using allyl pyrroles-2-methylaldiminate nickel(II); and FIG. 12 is an Auger Electron Spectrograph of a nickel film grown in PEALD mode at 400° C. using allyl pyrroles-2-methylaldiminate nickel(II).

DESCRIPTION OF PREFERRED EMBODIMENTS

Disclosed are metal-containing precursors having the formula:

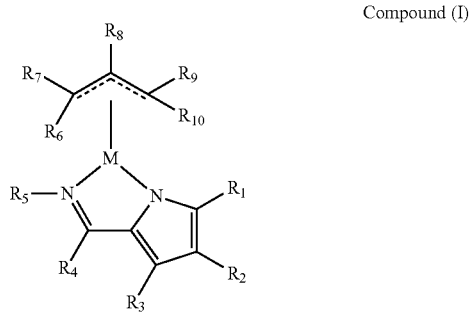

Compound (I)

wherein
M is a metal selected from the group consisting of Ni, Co, Mn, and Pd, preferably from Ni, Mn, and Pd, more preferably from Ni or Pd, and most preferably M is Ni; and
each of $R_1$, $R_2$, $R_3$, $R_4$, $R_5$, $R_6$, $R_7$, $R_8$, $R_9$, and $R_{10}$ are independently selected from H; a C1-C4 linear, branched, or cyclic alkyl group; a C1-C4 linear, branched, or cyclic alkylsilyl group (mono, bis, or tris alkyl); a C1-C4 linear, branched, or cyclic alkylamino group; or a C1-C4 linear, branched, or cyclic fluoroalkyl group (in which some or all of the substituents are F, i.e. partially or totally fluorinated); preferably each of $R_1$, $R_2$, $R_3$, $R_4$, $R_5$, $R_6$, $R_7$, $R_8$, $R_9$, and $R_{10}$ is selected from H or a C1-C4 linear or branched alkyl group.

Applicants believe that the allyl ligand promotes volatility and the pyrroles-2-aldiminate promotes thermal stability. As a result, the disclosed metal-containing precursors may have the following properties: i) liquid form or low melting point solid; ii) high volatility; iii) sufficient thermal stability to avoid decomposition during handling and delivery; and iv) appropriate reactivity during CVD/ALD process.

Suitable metal-containing precursors include (the chemical structure for each precursor is illustrated below by the associated reference letter):

A: (allyl)(2-iminemethylpyrrolyl) nickel(II)
B: (allyl)(2-methyliminemethylpyrrolyl) nickel (II)
C: (allyl)(2-ethyliminemethylpyrrolyl) nickel (II)
D: (allyl)(2-isopropyliminemethylpyrrolyl) nickel(II)
E: (allyl)(2-npropyliminemethylpyrrolyl) nickel (II)
F: (allyl)(2-nbutyliminemethylpyrrolyl) nickel (II)
G: (allyl)(2-secbutyliminemethylpyrrolyl) nickel (II)
H: (allyl)(2-isobutyliminemethylpyrrolyl) nickel (II)

I: (allyl)(2-tertbutyliminemethylpyrrolyl) nickel (II)
J: (allyl)(2-trimethylsilylbutyliminemethylpyrrolyl) nickel (II)
K: (1-Methylallyl)(2-iminemethylpyrrolyl) nickel(II)
L: (1-Methylallyl)(2-methyliminemethylpyrrolyl) nickel (II)
M: (1-Methylallyl)(2-ethyliminemethylpyrrolyl) nickel (II)
N: (1-Methylallyl)(2-isopropyliminemethylpyrrolyl) nickel (II)
O: (1-Methylallyl)(2-npropyliminemethylpyrrolyl) nickel (II)
P: (1-Methylallyl)(2-nbutyliminemethylpyrrolyl) nickel (II)
Q: (1-Methylallyl)(2-secbutyliminemethylpyrrolyl) nickel (II)
R: (1-Methylallyl)(2-isobutyliminemethylpyrrolyl) nickel (II)
S: (1-Methylallyl)(2-tertbutyliminemethylpyrrolyl) nickel (II)
T: (1-Methylallyl)(2-trimethylsilylbutyliminemethylpyrrolyl) nickel (II)
U: (2-Methylallyl)(2-iminemethylpyrrolyl) nickel(II)
V: (2-Methylallyl)(2-methyliminemethylpyrrolyl) nickel (II)
W: (2-Methylallyl)(2-ethyliminemethylpyrrolyl) nickel (II)
X: (2-Methylallyl)(2-isopropyliminemethylpyrrolyl) nickel (II)
Y: (2-Methylallyl)(2-npropyliminemethylpyrrolyl) nickel (II)
Z: (2-Methylallyl)(2-nbutyliminemethylpyrrolyl) nickel (II)
AA: (2-Methylallyl)(2-secbutyliminemethylpyrrolyl) nickel (II)
AB: (2-Methylallyl)(2-isobutyliminemethylpyrrolyl) nickel (II)
AC: (2-Methylallyl)(2-tertbutyliminemethylpyrrolyl) nickel (II)
AD: (2-Methylallyl)(2-trimethylsilylbutyliminemethylpyrrolyl) nickel (II)

A
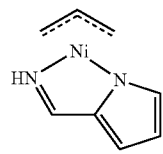

B
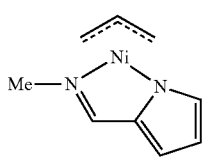

C
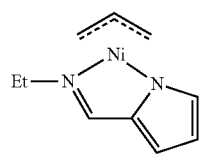

D
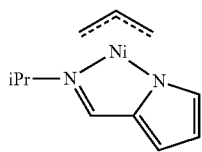

E
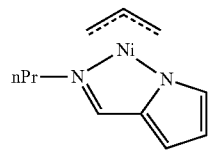

F
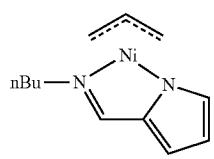

G
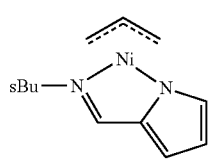

H
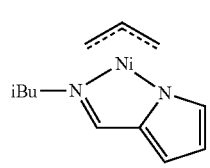

I
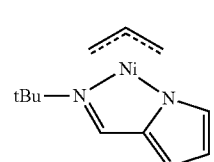

J
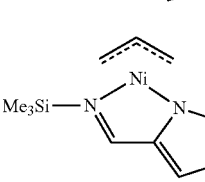

K
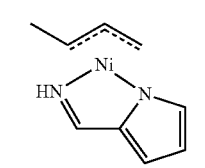

L
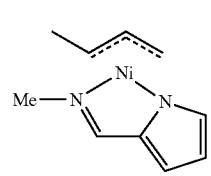

M
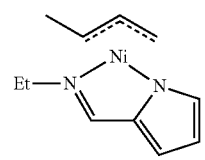

N
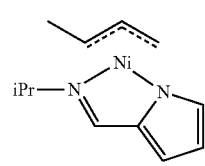

-continued

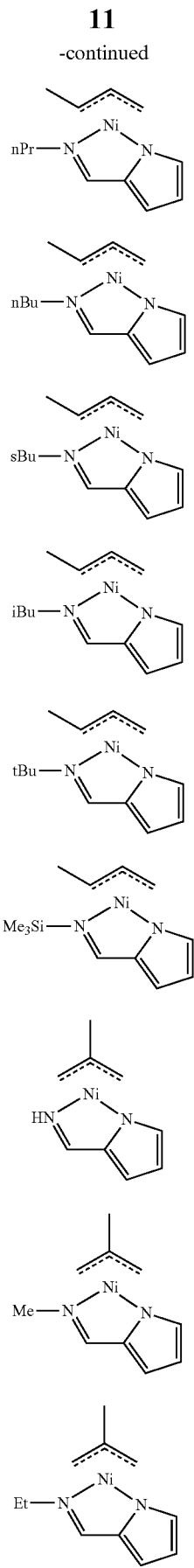

O
P
Q
R
S
T
U
V
W

-continued

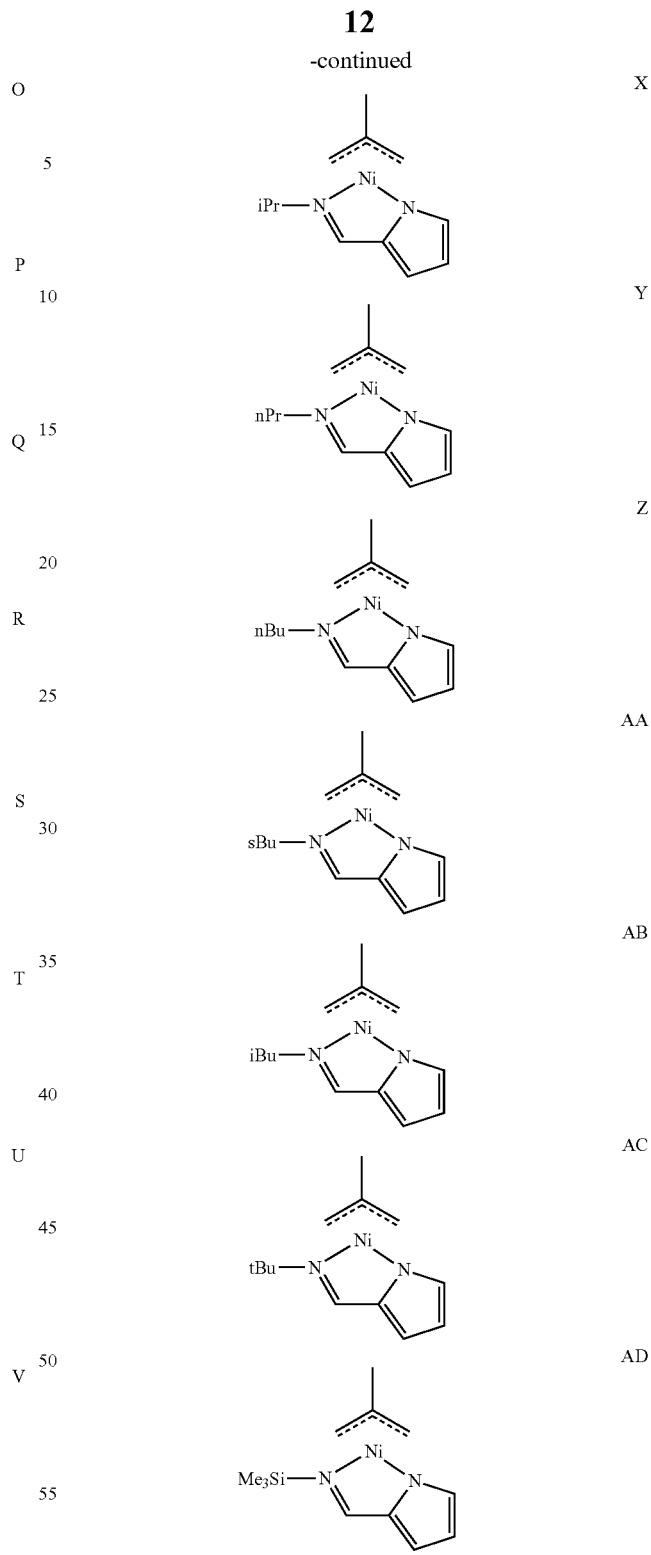

X
Y
Z
AA
AB
AC
AD

AE: (allyl)(2-iminemethylpyrrolyl) cobalt(II)
AF: (allyl)(2-methyliminemethylpyrrolyl) cobalt (II)
AG: (allyl)(2-ethyliminemethylpyrrolyl) cobalt (II)
AH: (allyl)(2-isopropyliminemethylpyrrolyl) cobalt (II)
AI: (allyl)(2-npropyliminemethylpyrrolyl) cobalt (II)
AJ: (allyl)(2-nbutyliminemethylpyrrolyl) cobalt (II)
AK: (allyl)(2-secbutyliminemethylpyrrolyl) cobalt (II)
AL: (allyl)(2-isobutyliminemethylpyrrolyl) cobalt (II)
AM: (allyl)(2-tertbutyliminemethylpyrrolyl) cobalt (II)

AN: (allyl)(2-trimethylsilylbutyliminemethylpyrrolyl) cobalt (II)
AO: (1-Methylallyl)(2-iminemethylpyrrolyl) cobalt (II)
AP: (1-Methylallyl)(2-methyliminemethylpyrrolyl) cobalt (II)
AQ: (1-Methylallyl)(2-ethyliminemethylpyrrolyl) cobalt (II)
AR: (1-Methylallyl)(2-isopropyliminemethylpyrrolyl) cobalt (II)
AS: (1-Methylallyl)(2-npropyliminemethylpyrrolyl) cobalt (II)
AT: (1-Methylallyl)(2-nbutyliminemethylpyrrolyl) cobalt (II)
AU: (1-Methylallyl)(2-secbutyliminemethylpyrrolyl) cobalt (II)
AV: (1-Methylallyl)(2-isobutyliminemethylpyrrolyl) cobalt (II)
AW: (1-Methylallyl)(2-tertbutyliminemethylpyrrolyl) cobalt (II)
AX: (1-Methylallyl)(2-trimethylsilylbutyliminemethylpyrrolyl) cobalt (II)
AY: (2-Methylallyl)(2-iminemethylpyrrolyl) cobalt (II)
BZ: (2-Methylallyl)(2-methyliminemethylpyrrolyl) cobalt (II)
BA: (2-Methylallyl)(2-ethyliminemethylpyrrolyl) cobalt (II)
BB: (2-Methylallyl)(2-isopropyliminemethylpyrrolyl) cobalt (II)
BC: (2-Methylallyl)(2-npropyliminemethylpyrrolyl) cobalt (II)
BD: (2-Methylallyl)(2-nbutyliminemethylpyrrolyl) cobalt (II)
BE: (2-Methylallyl)(2-secbutyliminemethylpyrrolyl) cobalt (II)
BF: (2-Methylallyl)(2-isobutyliminemethylpyrrolyl) cobalt (II)
BG: (2-Methylallyl)(2-tertbutyliminemethylpyrrolyl) cobalt (II)
BH: (2-Methylallyl)(2-trimethylsilylbutyliminemethylpyrrolyl) cobalt (II)

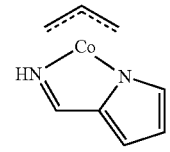

AE

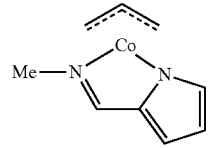

AF

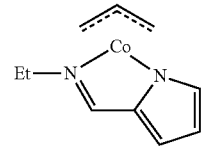

AG

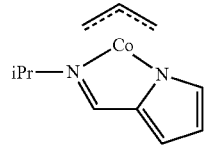

AH

-continued

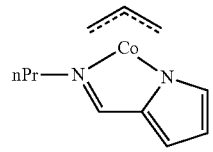

AI

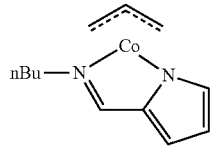

AJ

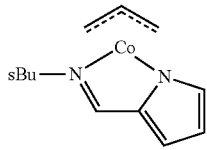

AK

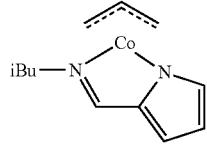

AL

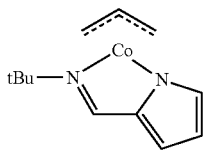

AM

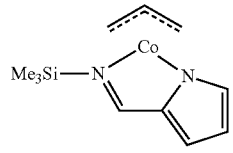

AN

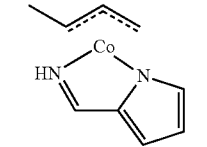

AO

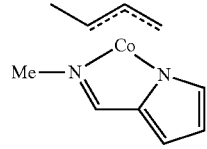

AP

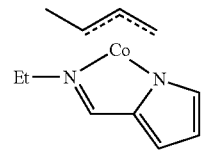

AQ

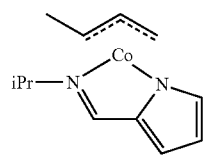

AR

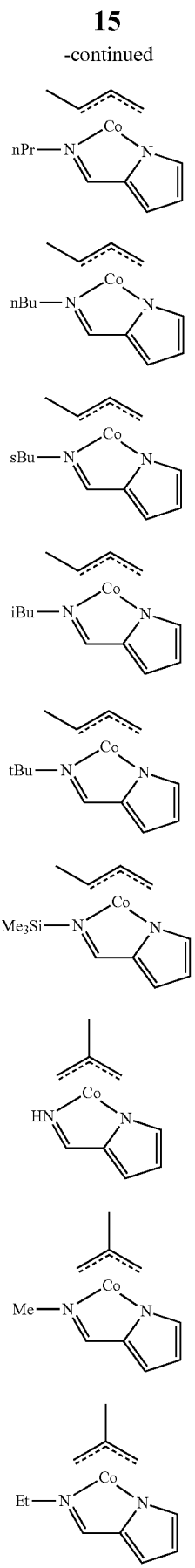
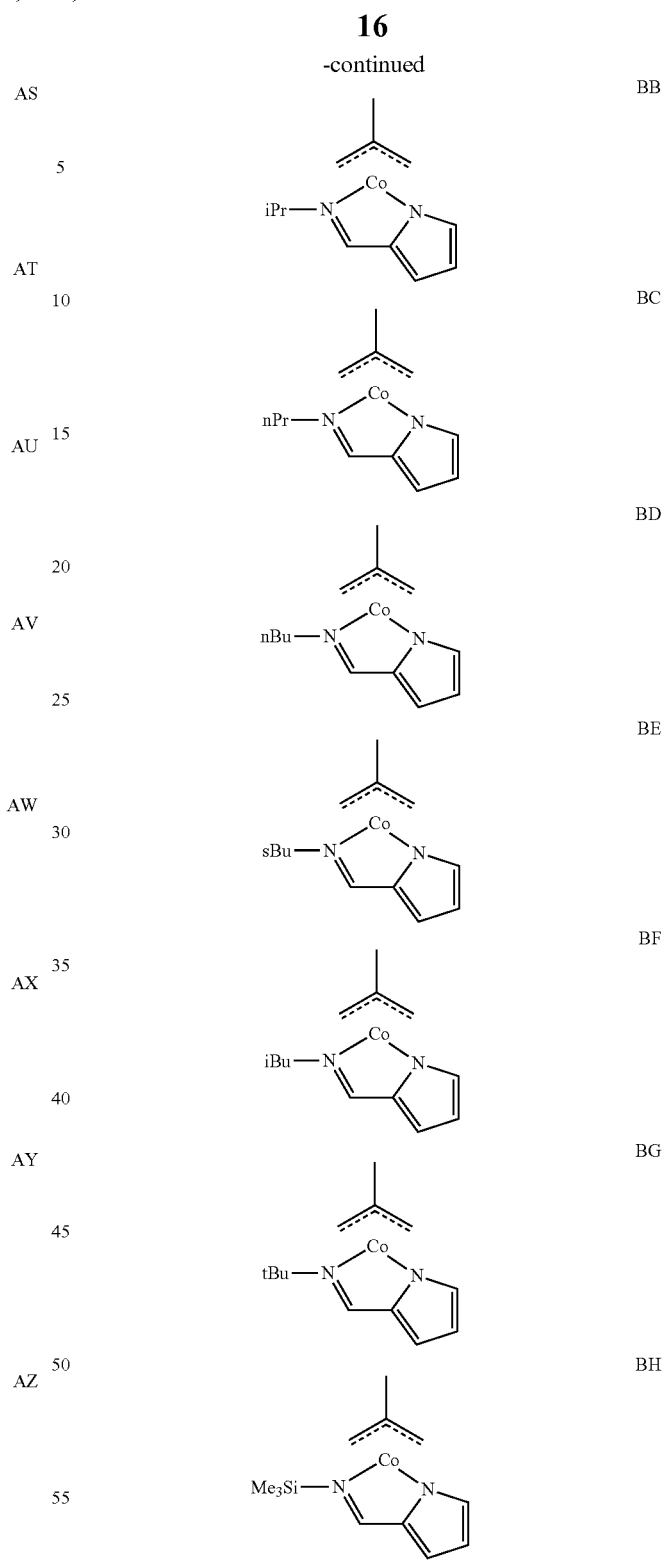

BJ: (allyl)(2-iminemethylpyrrolyl) manganese(II)
BK: (allyl)(2-methyliminemethylpyrrolyl) manganese (II)
BL: (allyl)(2-ethyliminemethylpyrrolyl) manganese (II)
BM: (allyl)(2-isopropyliminemethylpyrrolyl) manganese (II)
BN: (allyl)(2-npropyliminemethylpyrrolyl) manganese (II)
BO: (allyl)(2-nbutyliminemethylpyrrolyl) manganese (II)
BP: (allyl)(2-secbutyliminemethylpyrrolyl) manganese (II)

BQ: (allyl)(2-isobutyliminemethylpyrrolyl) manganese (II)
BR: (allyl)(2-tertbutyliminemethylpyrrolyl) manganese (II)
BS: (allyl)(2-trimethylsilylbutyliminemethylpyrrolyl) manganese (II)
BT: (1-Methylallyl)(2-iminemethylpyrrolyl) manganese (II)
BU: (1-Methylallyl)(2-methyliminemethylpyrrolyl) manganese (II)
BV: (1-Methylallyl)(2-ethyliminemethylpyrrolyl) manganese (II)
BW: (1-Methylallyl)(2-isopropyliminemethylpyrrolyl) manganese (II)
BX: (1-Methylallyl)(2-npropyliminemethylpyrrolyl) manganese (II)
BY: (1-Methylallyl)(2-nbutyliminemethylpyrrolyl) manganese (II)
BZ: (1-Methylallyl)(2-secbutyliminemethylpyrrolyl) manganese (II)
CA: (1-Methylallyl)(2-isobutyliminemethylpyrrolyl) manganese (II)
CB: (1-Methylallyl)(2-tertbutyliminemethylpyrrolyl) manganese (II)
CC: (1-Methylallyl)(2-trimethylsilylbutyliminemethylpyrrolyl) manganese (II)
CD: (2-Methylallyl)(2-iminemethylpyrrolyl) manganese (II)
CE: (2-Methylallyl)(2-methyliminemethylpyrrolyl) manganese (II)
CF: (2-Methylallyl)(2-ethyliminemethylpyrrolyl) manganese (II)
CG: (2-Methylallyl)(2-isopropyliminemethylpyrrolyl) manganese (II)
CH: (2-Methylallyl)(2-npropyliminemethylpyrrolyl) manganese (II)
CI: (2-Methylallyl)(2-nbutyliminemethylpyrrolyl) manganese (II)
CJ: (2-Methylallyl)(2-secbutyliminemethylpyrrolyl) manganese (II)
CK: (2-Methylallyl)(2-isobutyliminemethylpyrrolyl) manganese (II)
CL: (2-Methylallyl)(2-tertbutyliminemethylpyrrolyl) manganese (II)
CM: (2-Methylallyl)(2-trimethylsilylbutyliminemethylpyrrolyl) manganese (II)

BJ

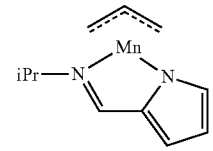

BM

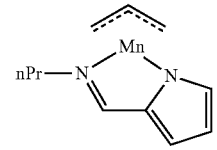

BN

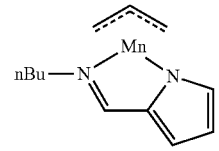

BO

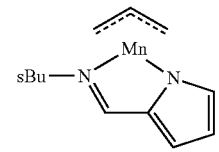

BP

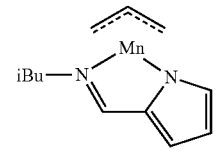

BQ

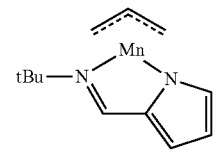

BR

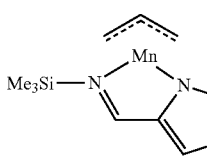

BS

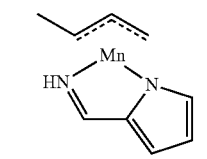

BT

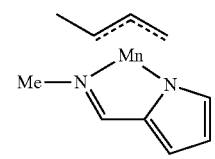

BU

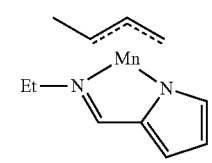

BV

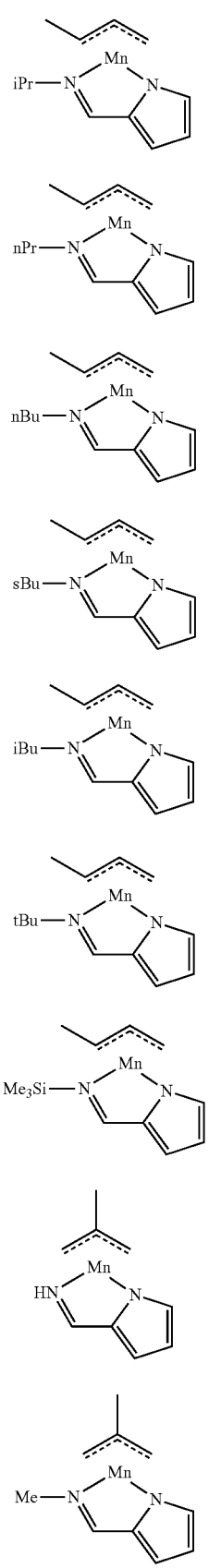
BW
BX
BY
BZ
CA
CB
CC
CD
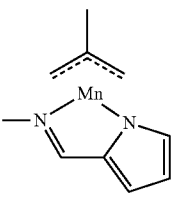 CF
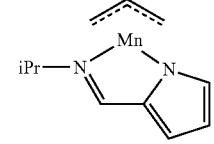 CG
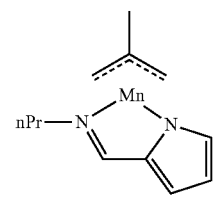 CH
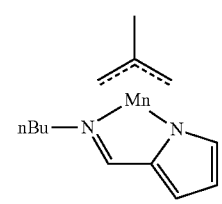 CI
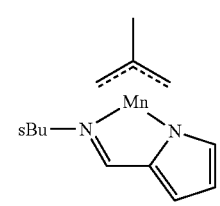 CJ
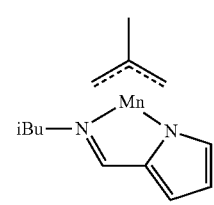 CK
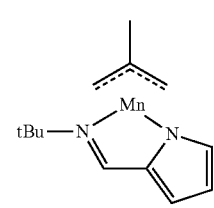 CL
CE
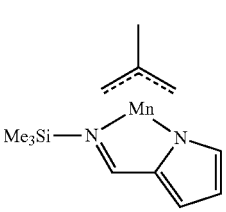 CM CN: (allyl)(2-iminemethylpyrrolyl) palladium(II)
CO: (allyl)(2-methyliminemethylpyrrolyl) palladium (II)
CP: (allyl)(2-ethyliminemethylpyrrolyl) palladium (II)
CQ: (allyl)(2-isopropyliminemethylpyrrolyl) palladium (II)
CR: (allyl)(2-npropyliminemethylpyrrolyl) palladium (II)
CS: (allyl)(2-nbutyliminemethylpyrrolyl) palladium (II)
CT: (allyl)(2-secbutyliminemethylpyrrolyl) palladium (II)
CU: (allyl)(2-isobutyliminemethylpyrrolyl) palladium (II)
CV: (allyl)(2-tertbutyliminemethylpyrrolyl) palladium (II)
CW: (allyl)(2-trimethylsilylbutyliminemethylpyrrolyl) palladium (II)
CX: (1-Methylallyl)(2-iminemethylpyrrolyl) palladium (II)
CY: (1-Methylallyl)(2-methyliminemethylpyrrolyl) palladium (II)
CZ: (1-Methylallyl)(2-ethyliminemethylpyrrolyl) palladium (II)
DA: (1-Methylallyl)(2-isopropyliminemethylpyrrolyl) palladium (II)
DB: (1-Methylallyl)(2-npropyliminemethylpyrrolyl) palladium (II)
DC: (1-Methylallyl)(2-nbutyliminemethylpyrrolyl) palladium (II)
DD: (1-Methylallyl)(2-secbutyliminemethylpyrrolyl) palladium (II)
DE: (1-Methylallyl)(2-isobutyliminemethylpyrrolyl) palladium (II)
DF: (1-Methylallyl)(2-tertbutyliminemethylpyrrolyl) palladium (II)
DG: (1-Methylallyl)(2-trimethylsilylbutyliminemethylpyrrolyl) palladium (II)
DH: (2-Methylallyl)(2-iminemethylpyrrolyl) palladium (II)
DI: (2-Methylallyl)(2-methyliminemethylpyrrolyl) palladium (II)
DJ: (2-Methylallyl)(2-ethyliminemethylpyrrolyl) palladium (II)
DK: (2-Methylallyl)(2-isopropyliminemethylpyrrolyl) palladium (II)
DL: (2-Methylallyl)(2-npropyliminemethylpyrrolyl) palladium (II)
DM: (2-Methylallyl)(2-nbutyliminemethylpyrrolyl) palladium (II)
DN: (2-Methylallyl)(2-secbutyliminemethylpyrrolyl) palladium (II)
DO: (2-Methylallyl)(2-isobutyliminemethylpyrrolyl) palladium (II)
DP: (2-Methylallyl)(2-tertbutyliminemethylpyrrolyl) palladium (II)
DQ: (2-Methylallyl)(2-trimethylsilylbutyliminemethylpyrrolyl) palladium (II)

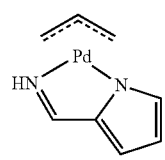

CN

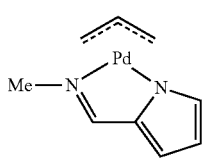

CO

-continued

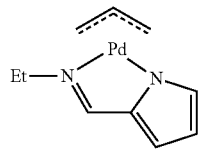

CP

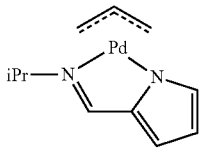

CQ

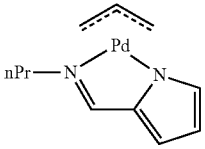

CR

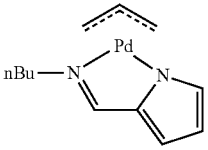

CS

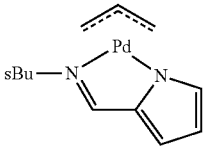

CT

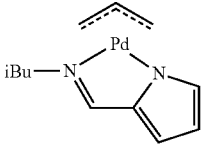

CU

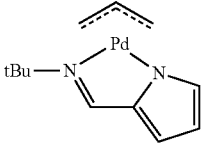

CV

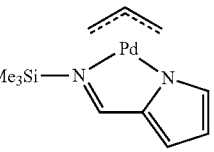

CW

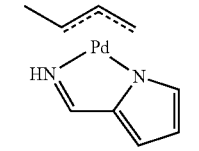

CX

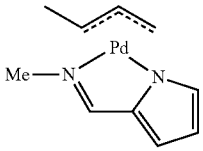

CY

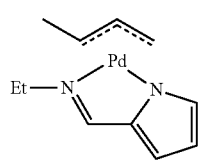 CZ
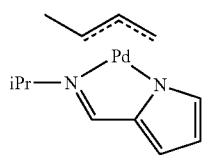 DA
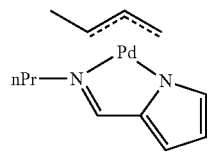 DB
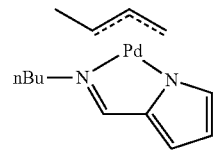 DC
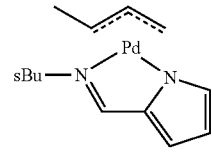 DD
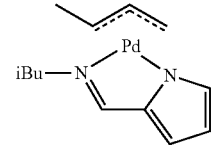 DE
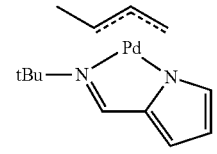 DF
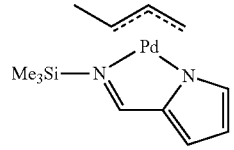 DG
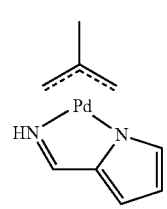 DH
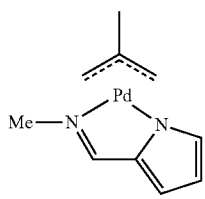 DI
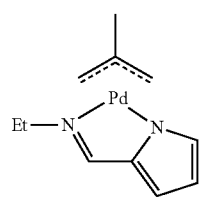 DJ
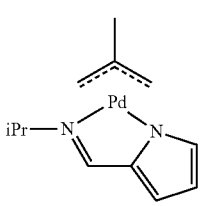 DK
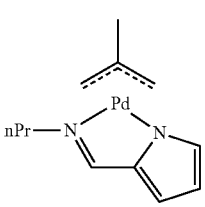 DL
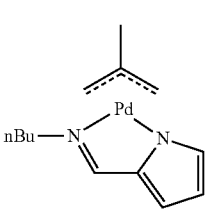 DM
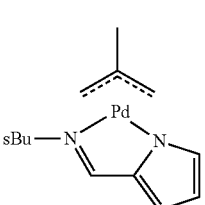 DN
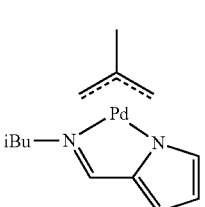 DO
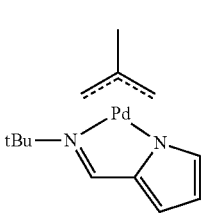 DP

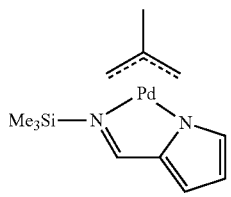

Preferably, the metal-containing precursor is 2-methylallyl 2-isopropyliminemethylpyrrolyl nickel(II) (with $R_1$ to $R_4$=H; $R_5$=iPr; $R_6$, $R_7$, $R_9$, $R_{10}$=H; and $R_8$=Me in Formula 1) due to its excellent vaporization results in atmospheric thermogravimetric analysis, leaving a small amount of final residue.

The disclosed metal-containing precursors may be synthesized by reacting lithium alkyliminealkylpyrrolyl with metal allyl chloride in a suitable solvent, such as THF and hexane. Some exemplary synthesis methods containing further details are provided in the Examples that follow.

Also disclosed are methods for forming a metal-containing layer on a substrate using a vapor deposition process. The method may be useful in the manufacture of semiconductor, photovoltaic, LCD-TFT, or flat panel type devices. The disclosed metal-containing precursors may be used to deposit thin metal-containing films using any deposition methods known to those of skill in the art. Examples of suitable deposition methods include without limitation, conventional chemical vapor deposition (CVD), plasma enhanced chemical vapor deposition (PECVD), low pressure chemical vapor deposition (LPCVD), plasma enhanced chemical vapor depositions (PECVD), atomic layer deposition (ALD), pulsed chemical vapor deposition (PCVD), plasma enhanced atomic layer deposition (PEALD), or combinations thereof.

The disclosed metal-containing precursors may be supplied either in neat form or in a blend with a suitable solvent, such as ethyl benzene, xylene, mesitylene, decane, dodecane. The disclosed precursors may be present in varying concentrations in the solvent.

One or more of the neat or blended metal-containing precursors are introduced into a reactor in vapor form by conventional means, such as tubing and/or flow meters. The precursor in vapor form may be produced by vaporizing the neat or blended precursor solution through a conventional vaporization step such as direct vaporization, distillation, or by bubbling. The neat or blended precursor may be fed in liquid state to a vaporizer where it is vaporized before it is introduced into the reactor. Alternatively, the neat or blended precursor may be vaporized by passing a carrier gas into a container containing the precursor or by bubbling the carrier gas into the precursor. The carrier gas may include, but is not limited to, Ar, He, $N_2$, and mixtures thereof. Bubbling with a carrier gas may also remove any dissolved oxygen present in the neat or blended precursor solution. The carrier gas and precursor are then introduced into the reactor as a vapor.

If necessary, the container of disclosed precursor may be heated to a temperature that permits the precursor to be in its liquid phase and to have a sufficient vapor pressure. The container may be maintained at temperatures in the range of, for example, approximately 0° C. to approximately 150° C. Those skilled in the art recognize that the temperature of the container may be adjusted in a known manner to control the amount of precursor vaporized.

The reactor may be any enclosure or chamber within a device in which deposition methods take place such as without limitation, a parallel-plate type reactor, a cold-wall type reactor, a hot-wall type reactor, a single-wafer reactor, a multi-wafer reactor, or other types of deposition systems under conditions suitable to cause the precursors to react and form the layers.

Generally, the reactor contains one or more substrates onto which the thin films will be deposited. The one or more substrates may be any suitable substrate used in semiconductor, photovoltaic, flat panel, or LCD-TFT device manufacturing. Examples of suitable substrates include without limitation, silicon substrates, silica substrates, silicon nitride substrates, silicon oxy nitride substrates, tungsten substrates, or combinations thereof. Additionally, substrates comprising tungsten or noble metals (e.g. platinum, palladium, rhodium, or gold) may be used. The substrate may also have one or more layers of differing materials already deposited upon it from a previous manufacturing step.

The temperature and the pressure within the reactor are held at conditions suitable for ALD or CVD depositions. In other words, after introduction of the vaporized precursor into the chamber, conditions within the chamber are such that at least part of the vaporized precursor is deposited onto the substrate to form a metal-containing film. For instance, the pressure in the reactor may be held between about 1 Pa and about $10^5$ Pa, more preferably between about 25 Pa and about $10^3$ Pa, as required per the deposition parameters. Likewise, the temperature in the reactor may be held between about 100° C. and about 500° C., preferably between about 150° C. and about 350° C.

The temperature of the reactor may be controlled by either controlling the temperature of the substrate holder or controlling the temperature of the reactor wall. Devices used to heat the substrate are known in the art. The reactor wall is heated to a sufficient temperature to obtain the desired film at a sufficient growth rate and with desired physical state and composition. A non-limiting exemplary temperature range to which the reactor wall may be heated includes from approximately 100° C. to approximately 500° C. When a plasma deposition process is utilized, the deposition temperature may range from approximately 150° C. to approximately 350° C. Alternatively, when a thermal process is performed, the deposition temperature may range from approximately 200° C. to approximately 500° C.

In addition to the disclosed precursor, a reactant may also be introduced into the reactor. The reactant may be an oxidizing gas such as one of $O_2$, $O_3$, $H_2O$, $H_2O_2$, oxygen containing radicals such as 0° or OH°, NO, $NO_2$, carboxylic acids, formic acid, acetic acid, propionic acid, and mixtures thereof. Preferably, the oxidizing gas is selected from the group consisting of $O_2$, $O_3$, $H_2O$, $H_2O_2$, oxygen containing radicals thereof such as 0° or OH°, and mixtures thereof. Alternatively, the reactant may be a reducing gas such as one of $H_2$, $NH_3$, $SiH_4$, $Si_2H_6$, $Si_3H_8$, $(CH_3)_2SiH_2$, $(C_2H_5)_2SiH_2$, $(CH_3)SiH_3$, $(C_2H_5)SiH_3$, phenyl silane, $N_2H_4$, $N(SiH_3)_3$, $N(CH_3)H_2$, $N(C_2H_5)H_2$, $N(CH_3)_2H$, $N(C_2H_5)_2H$, $N(CH_3)_3$, $N(C_2H_5)_3$, $(SiMe_3)_2NH$, $(CH_3)HNNH_2$, $(CH_3)_2NNH_2$, phenyl hydrazine, N-containing molecules, $B_2H_6$, 9-borabicyclo[3,3,1]nonane, dihydrobenzenfuran, pyrazoline, trimethylaluminium, dimethylzinc, diethylzinc, radical species thereof, and mixtures thereof. Preferably, the reducing as is $H_2$, $NH_3$, $SiH_4$, $Si_2H_6$, $Si_3H_8$, $SiH_2Me_2$, $SiH_2Et_2$, $N(SiH_3)_3$, hydrogen radicals thereof, or mixtures thereof.

The reactant may be treated by a plasma, in order to decompose the reactant into its radical form. $N_2$ may also be utilized as a reducing gas when treated with plasma. For instance, the plasma may be generated with a power ranging from about 50 W to about 500 W, preferably from about 100 W to about 200 W. The plasma may be generated or present within the reactor itself. Alternatively, the plasma may generally be at a location removed from the reactor, for instance, in a remotely located plasma system. One of skill in the art will recognize methods and apparatus suitable for such plasma treatment.

The vapor deposition conditions within the chamber allow the disclosed precursor and the reactant to react and form a metal-containing film on the substrate. In some embodiments, Applicants believe that plasma-treating the reactant may provide the reactant with the energy needed to react with the disclosed precursor.

Depending on what type of film is desired to be deposited, a second precursor may be introduced into the reactor. The second precursor comprises another metal source, such as copper, praseodymium, manganese, ruthenium, titanium, tantalum, bismuth, zirconium, hafnium, lead, niobium, magnesium, aluminum, lanthanum, or mixtures of these. When a second metal containing precursor is utilized, the resultant film deposited on the substrate may contain at least two different metal types.

The metal-containing precursors and reactants may be introduced into the reactor either simultaneously (chemical vapor deposition), sequentially (atomic layer deposition) or different combinations thereof. The reactor may be purged with an inert gas between the introduction of the precursor and the introduction of the reactant. Alternatively, the reactant and the precursor may be mixed together to form a reactant/precursor mixture, and then introduced to the reactor in mixture form. Another example is to introduce the reactant continuously and to introduce the at least one metal-containing precursor by pulse (pulsed chemical vapor deposition).

The vaporized precursor and the reactant may be pulsed sequentially or simultaneously (e.g. pulsed CVD) into the reactor. Each pulse of precursor may last for a time period ranging from about 0.01 seconds to about 10 seconds, alternatively from about 0.3 seconds to about 3 seconds, alternatively from about 0.5 seconds to about 2 seconds. In another embodiment, the reactant may also be pulsed into the reactor. In such embodiments, the pulse of each gas may last for a time period ranging from about 0.01 seconds to about 10 seconds, alternatively from about 0.3 seconds to about 3 seconds, alternatively from about 0.5 seconds to about 2 seconds.

Depending on the particular process parameters, deposition may take place for a varying length of time. Generally, deposition may be allowed to continue as long as desired or necessary to produce a film with the necessary properties. Typical film thicknesses may vary from several angstroms to several hundreds of microns, depending on the specific deposition process. The deposition process may also be performed as many times as necessary to obtain the desired film.

In one non-limiting exemplary CVD type process, the vapor phase of the disclosed metal-containing precursor and a reactant are simultaneously introduced into the reactor. The two react to form the resulting metal-containing thin film. When the reactant in this exemplary CVD process is treated with a plasma, the exemplary CVD process becomes an exemplary PECVD process. The reactant may be treated with plasma prior or subsequent to introduction into the chamber.

In one non-limiting exemplary ALD type process, the vapor phase of the disclosed metal-containing precursor is introduced into the reactor, where it is contacted with a suitable substrate. Excess precursor may then be removed from the reactor by purging and/or evacuating the reactor. A reducing gas (for example, $H_2$) is introduced into the reactor where it reacts with the absorbed precursor in a self-limiting manner. Any excess reducing gas is removed from the reactor by purging and/or evacuating the reactor. If the desired film is a metal film, this two-step process may provide the desired film thickness or may be repeated until a film having the necessary thickness has been obtained.

Alternatively, if the desired film is a bimetal film, the two-step process above may be followed by introduction of the vapor of a second metal-containing precursor into the reactor. The second metal-containing precursor will be selected based on the nature of the bimetal film being deposited. After introduction into the reactor, the second metal-containing precursor is contacted with the substrate. Any excess second metal-containing precursor is removed from the reactor by purging and/or evacuating the reactor. Once again, a reducing gas may be introduced into the reactor to react with the second metal-containing precursor. Excess reducing gas is removed from the reactor by purging and/or evacuating the reactor. If a desired film thickness has been achieved, the process may be terminated. However, if a thicker film is desired, the entire four-step process may be repeated. By alternating the provision of the metal-containing precursor, second metal-containing precursor, and reactant, a film of desired composition and thickness can be deposited.

When the reactant in this exemplary ALD process is treated with a plasma, the exemplary ALD process becomes an exemplary PEALD process. The co-reactant may be treated with plasma prior or subsequent to introduction into the chamber.

The metal-containing films resulting from the processes discussed above may include a pure metal (M), metal silicide ($M_kSi_l$), or metal oxide ($M_nO_m$) film wherein M is Ni, Co, Mn, and Pd and k, l, m, n, x, y, and z are integers which inclusively range from 1 to 6. One of ordinary skill in the art will recognize that by judicial selection of the appropriate disclosed precursor, optional second metal-containing precursors, and co-reactant species, the desired film composition may be obtained.

EXAMPLES

The following examples illustrate experiments performed in conjunction with the disclosure herein. The examples are not intended to be all inclusive and are not intended to limit the scope of disclosure described herein.

Example 1

Synthesis of allyl 2-isopropyliminemethylpyrrolyl nickel(II)

2.0 g (9.1 mmol) of $NiCl_2$(DME) and 10 mL THF were introduced under nitrogen in a Schlenk flask. 4.55 mL (9.1 mmol) of allylmagnesium chloride (2M solution in THF) was introduced slowly at 0° C. The mixture was stirred for overnight at room temperature. A brown suspension was obtained.

1.240 g (9.1 mmol) of 2-isopropyliminemethylpyrrole was introduced in a Schlenk flask. nBuLi 3.65 mL (2.5M in hexane) was introduced at −78° C. and stirred 1 h at room temperature.

The lithium 2-isopropyliminemethylpyrrolyl solution was added to the nickel suspension and stirred overnight at room temperature.

A brown solution was formed. Solvent were removed under vacuum and toluene added (20 mL). The solution was filtered over a diatomaceous earth filter medium sold by Kanto Chemical Co. under the trademark Celite®. The solvent was then removed under vacuum. The solid was sublimed at 60-90° C. @ 50 mTorr. 760 mg (35% mol/mol yield) of a yellow solid was recovered. Mp=74° C. NMR 1H in $C_6D_6$ is displayed in FIG. 1.

Example 2

Synthesis of 1-methylallyl 2-isopropylimine methylpyrrolyl nickel(II)

2.0 g (9.1 mmol) of $NiCl_2$(DME) and 10 mL THF were introduced under nitrogen in a Schlenk flask. 18.2 mL (9.1 mmol) of 2-butenylmagnesium chloride (0.5 M solution in THF) was introduced slowly at 0° C. The mixture was stirred for overnight at room temperature. A red-brown suspension was obtained.

1.240 g (9.1 mmol) of 2-isopropyliminemethylpyrrole was introduced in a Schlenk flask. nBuLi 5.45 mL (1.67M in hexane) was introduced at −78° C. and stirred 1 h at room temperature.

The lithium 2-isopropyliminemethylpyrrolyl solution was added to the nickel suspension and stirred overnight at room temperature.

A brown solution was formed. Solvent were removed under vacuum and toluene added (20 mL). The solution was filtered over a diatomaceous earth filter medium sold by Kanto Chemical Co. under the trademark Celite®. The solvent was then removed under vacuum. The solid was sublimed at 90° C. @ 50 mTorr. 930 mg (41% mol/mol yield) of a yellow solid was recovered. Melting point=73° C.

Example 3

Synthesis of 2-methylallyl 2-isopropylimine methylpyrrolyl nickel(II)

2.0 g (9.1 mmol) of $NiCl_2$(DME) and 10 mL THF were introduced under nitrogen in a Schlenk flask. 18.2 mL (9.1 mmol) of 2-methylallylmagnesium chloride (0.5M solution in THF) was introduced slowly at 0° C. The mixture was stirred for overnight at room temperature. A red-brown suspension was obtained.

1.240 g (9.1 mmol) of 2-isopropyliminemethylpyrrole was introduced in a Schlenk flask. nBuLi 5.45 mL (1.67M in hexane) was introduced at −78° C. and stirred 1 h at room temperature.

The lithium 2-isopropyliminemethylpyrrolyl solution was added to the nickel suspension and stirred overnight at room temperature.

A brown solution was formed. Solvent were removed under vacuum and toluene added (20 mL). The solution was filtered over a diatomaceous earth filter medium sold by Kanto Chemical Co. under the trademark Celite®. The solvent was then removed under vacuum. The solid was sublimed at 100° C. @ 50 mTorr. 760 mg (33% mol/mol yield) of a yellow brown solid was recovered. Melting point=58° C. NMR 1H in $C_6D_6$ is displayed in FIG. 2.

Example 4

Synthesis of allyl 2-ethylimine methylpyrrolyl nickel(II)

2.0 g (9.1 mmol) of $NiCl_2$(DME) and 10 mL THF were introduced under nitrogen in a Schlenk flask. 4.55 mL (9.1 mmol) of allylmagnesium chloride (2M solution in THF) was introduced slowly at 0° C. The mixture was stirred for overnight at room temperature. A brown suspension was obtained.

1.110 g (9.1 mmol) of 2-ethyliminemethylpyrrole was introduced in a Schlenk flask. nBuLi 5.45 mL (1.67M in hexane) was introduced at −78° C. and stirred 1 h at room temperature.

The lithium 2-ethyliminemethylpyrrolyl solution was added to the nickel suspension and stirred overnight at room temperature.

A brown solution was formed. Solvent were removed under vacuum and toluene added (20 mL). The solution was filtered over a diatomaceous earth filter medium sold by Kanto Chemical Co. under the trademark Celite®. The solvent was then removed under vacuum. The solid was sublimed at 90° C. @ 100 mTorr. 560 mg (28% mol/mol yield) of a yellow brown solid was recovered. Mp=47° C. NMR 1H in $C_6D_6$ is displayed in FIG. 3.

Example 5

Synthesis of 2-methylallyl 2-ethylimine methylpyrrolyl nickel(II)

2.0 g (9.1 mmol) of $NiCl_2$(DME) and 10 mL THF were introduced under nitrogen in a Schlenk flask. 18.2 mL (9.1 mmol) of 2-methylallylmagnesium chloride (0.5M solution in THF) was introduced slowly at 0° C. The mixture was stirred for overnight at room temperature. A red-brown suspension was obtained.

1.110 g (9.1 mmol) of 2-ethyliminemethylpyrrole was introduced in a Schlenk flask. nBuLi 5.45 mL (1.67M in hexane) was introduced at −78° C. and stirred 1 h at room temperature.

The lithium 2-ethyliminemethylpyrrolyl solution was added to the nickel suspension and stirred overnight at room temperature.

A brown solution was formed. Solvent were removed under vacuum and toluene added (20 mL). The solution was filtered over a diatomaceous earth filter medium sold by Kanto Chemical Co. under the trademark Celite®. The solvent was then removed under vacuum. The solid was sublimed at 90° C. @ 50 mTorr. 450 mg (21% mol/mol yield) of a yellow brown solid was recovered. Mp=61° C. NMR 1H in $C_6D_6$ is displayed in FIG. 4.

Example 6

Thermogravimetric Analysis (TGA) of allyl 2-alkyliminemethylpyrrolyl nickel(II) precursors TGA testing was performed using a TGA/SDTA851 from Mettler Toledo in a glove box under pure nitrogen atmosphere. A nitrogen flow rate of 100 sccm was applied. The temperature was increased by 10° C./min under atmospheric or vacuum (20 mbar) conditions.

The precursors of Examples 1-5 were fully vaporized under vacuum condition (FIG. 5 to FIG. 9). All were found to have a clean evaporation under vacuum TGA condition. 2-methylallyl 2-isopropyliminemethylpyrrolyl nickel(II) ($R_1$ to $R_4$=H and $R_5$=iPr, $R_6$, $R_7$, $R_9$, $R_{10}$=H and $R_8$=Me) (FIG. 7) in particular could be vaporized in atmospheric TGA with a small amount of final residue. The vapor pressure of allyl pyrroles-2-methylaldiminate nickel(II) precursors are about 133.32 Pa @ 130° C. which makes those precursor suitable for ALD applications (FIG. 10).

Example 7

Deposition of pure nickel films by PEALD allyl 2-isopropyliminemethylpyrrolyl nickel(II) precursor PEALD tests were performed using allyl 2-isopropylimine methylpyrrolyl nickel(II), which was placed in a vessel heated to 100° C. Typical PEALD conditions were used, such as using hydrogen/ammonia (1/1) plasma with a reactor pressure fixed at ~1 Torr and plasma power set to 200 W. ALD behavior with complete surface saturation and reaction was assessed at 300 and 350° C. FIG. 11 is a graph of the resulting nickel film deposition rate as a function of precursor pulse time. A deposition rate as high as 0.73 Å/cycle was obtained at 300° C.

Auger Electron Spectroscopy (AES) of the resulting nickel film showed no carbon or nitrogen incorporation into the film at 350 and 400° C. (FIG. 12).

It will be understood that many additional changes in the details, materials, steps, and arrangement of parts, which have been herein described and illustrated in order to explain the nature of the invention, may be made by those skilled in the art within the principle and scope of the invention as expressed in the appended claims. Thus, the present invention is not intended to be limited to the specific embodiments in the examples given above and/or the attached drawings.

We claim:
1. A metal-containing precursor having the formula:

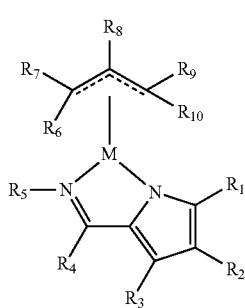

Compound (I)

wherein
M is a metal selected from the group consisting of Ni, Co, Mn, and Pd; and
each of $R_1$, $R_2$, $R_3$, $R_4$, $R_5$, $R_6$, $R_7$, $R_8$, $R_9$, and $R_{10}$ are independently selected from H; a C1-C4 linear, branched, or cyclic alkyl group; a C1-C4 linear, branched, or cyclic alkylsilyl group (mono, bis, or tris alkyl); a C1-C4 linear, branched, or cyclic alkylamino group; or a C1-C4 linear, branched, or cyclic fluoroalkyl group.

2. The metal-containing precursor of claim 1, wherein the metal-containing precursor is selected from the group consisting of
(allyl)(2-iminemethylpyrrolyl) nickel(II);
(allyl)(2-methyliminemethylpyrrolyl) nickel (II);
(allyl)(2-ethyliminemethylpyrrolyl) nickel (II);
(allyl)(2-isopropyliminemethylpyrrolyl) nickel(II);
(allyl)(2-npropyliminemethylpyrrolyl) nickel (II);
(allyl)(2-nbutyliminemethylpyrrolyl) nickel (II);
(allyl)(2-secbutyliminemethylpyrrolyl) nickel (II);
(allyl)(2-isobutyliminemethylpyrrolyl) nickel (II);
(allyl)(2-tertbutyliminemethylpyrrolyl) nickel (II);
(allyl)(2-trimethylsilylbutyliminemethylpyrrolyl) nickel (II);
(1-Methylallyl)(2-iminemethylpyrrolyl) nickel(II);
(1-Methylallyl)(2-methyliminemethylpyrrolyl) nickel (II);
(1-Methylallyl)(2-ethyliminemethylpyrrolyl) nickel (II);
(1-Methylallyl)(2-isopropyliminemethylpyrrolyl) nickel (II);
(1-Methylallyl)(2-npropyliminemethylpyrrolyl) nickel (II);
(1-Methylallyl)(2-nbutyliminemethylpyrrolyl) nickel (II);
(1-Methylallyl)(2-secbutyliminemethylpyrrolyl) nickel (II);
(1-Methylallyl)(2-isobutyliminemethylpyrrolyl) nickel (II);
(1-Methylallyl)(2-tertbutyliminemethylpyrrolyl) nickel (II);
(1-Methylallyl)(2-trimethylsilylbutyliminemethylpyrrolyl) nickel (II);
(2-Methylallyl)(2-iminemethylpyrrolyl) nickel(II);
(2-Methylallyl)(2-methyliminemethylpyrrolyl) nickel (II);
(2-Methylallyl)(2-ethyliminemethylpyrrolyl) nickel (II);
(2-Methylallyl)(2-isopropyliminemethylpyrrolyl) nickel (II);
(2-Methylallyl)(2-npropyliminemethylpyrrolyl) nickel (II);
(2-Methylallyl)(2-nbutyliminemethylpyrrolyl) nickel (II);
(2-Methylallyl)(2-secbutyliminemethylpyrrolyl) nickel (II);
(2-Methylallyl)(2-isobutyliminemethylpyrrolyl) nickel (II);
(2-Methylallyl)(2-tertbutyliminemethylpyrrolyl) nickel (II);
(2-Methylallyl)(2-trimethylsilylbutyliminemethylpyrrolyl) nickel (II);
(allyl)(2-iminemethylpyrrolyl) cobalt(II);
(allyl)(2-methyliminemethylpyrrolyl) cobalt (II);
(allyl)(2-ethyliminemethylpyrrolyl) cobalt (II);
(allyl)(2-isopropyliminemethylpyrrolyl) cobalt (II);
(allyl)(2-npropyliminemethylpyrrolyl) cobalt (II);
(allyl)(2-nbutyliminemethylpyrrolyl) cobalt (II);
(allyl)(2-secbutyliminemethylpyrrolyl) cobalt (II);
(allyl)(2-isobutyliminemethylpyrrolyl) cobalt (II);
(allyl)(2-tertbutyliminemethylpyrrolyl) cobalt (II);
(allyl)(2-trimethylsilylbutyliminemethylpyrrolyl) cobalt (II);
(1-Methylallyl)(2-iminemethylpyrrolyl) cobalt (II);
(1-Methylallyl)(2-methyliminemethylpyrrolyl) cobalt (II);
(1-Methylallyl)(2-ethyliminemethylpyrrolyl) cobalt (II);
(1-Methylallyl)(2-isopropyliminemethylpyrrolyl) cobalt (II);
(1-Methylallyl)(2-npropyliminemethylpyrrolyl) cobalt (II);
(1-Methylallyl)(2-nbutyliminemethylpyrrolyl) cobalt (II);
(1-Methylallyl)(2-secbutyliminemethylpyrrolyl) cobalt (II);
(1-Methylallyl)(2-isobutyliminemethylpyrrolyl) cobalt (II);
(1-Methylallyl)(2-tertbutyliminemethylpyrrolyl) cobalt (II);
(1-Methylallyl)(2-trimethylsilylbutyliminemethylpyrrolyl) cobalt (II);
(2-Methylallyl)(2-iminemethylpyrrolyl) cobalt (II);
(2-Methylallyl)(2-methyliminemethylpyrrolyl) cobalt (II);
(2-Methylallyl)(2-ethyliminemethylpyrrolyl) cobalt (II);
(2-Methylallyl)(2-isopropyliminemethylpyrrolyl) cobalt (II);
(2-Methylallyl)(2-npropyliminemethylpyrrolyl) cobalt (II);
(2-Methylallyl)(2-nbutyliminemethylpyrrolyl) cobalt (II);
(2-Methylallyl)(2-secbutyliminemethylpyrrolyl) cobalt (II);

(2-Methylallyl)(2-isobutyliminemethylpyrrolyl) cobalt (II);
(2-Methylallyl)(2-tertbutyliminemethylpyrrolyl) cobalt (II);
(2-Methylallyl)(2-trimethylsilylbutyliminemethylpyrrolyl) cobalt (II);
(allyl)(2-iminemethylpyrrolyl) manganese(II);
(allyl)(2-methyliminemethylpyrrolyl) manganese (II);
(allyl)(2-ethyliminemethylpyrrolyl) manganese (II);
(allyl)(2-isopropyliminemethylpyrrolyl) manganese (II);
(allyl)(2-npropyliminemethylpyrrolyl) manganese (II);
(allyl)(2-nbutyliminemethylpyrrolyl) manganese (II);
(allyl)(2-secbutyliminemethylpyrrolyl) manganese (II);
(allyl)(2-isobutyliminemethylpyrrolyl) manganese (II);
(allyl)(2-tertbutyliminemethylpyrrolyl) manganese (II);
(allyl)(2-trimethylsilylbutyliminemethylpyrrolyl) manganese (II);
(1-Methylallyl)(2-iminemethylpyrrolyl) manganese (II);
(1-Methylallyl)(2-methyliminemethylpyrrolyl) manganese (II);
(1-Methylallyl)(2-ethyliminemethylpyrrolyl) manganese (II);
(1-Methylallyl)(2-isopropyliminemethylpyrrolyl) manganese (II);
(1-Methylallyl)(2-npropyliminemethylpyrrolyl) manganese (II);
(1-Methylallyl)(2-nbutyliminemethylpyrrolyl) manganese (II);
(1-Methylallyl)(2-secbutyliminemethylpyrrolyl) manganese (II);
(1-Methylallyl)(2-isobutyliminemethylpyrrolyl) manganese (II);
(1-Methylallyl)(2-tertbutyliminemethylpyrrolyl) manganese (II);
(1-Methylallyl)(2-trimethylsilylbutyliminemethylpyrrolyl) manganese (II);
(2-Methylallyl)(2-iminemethylpyrrolyl) manganese (II);
(2-Methylallyl)(2-methyliminemethylpyrrolyl) manganese (II);
(2-Methylallyl)(2-ethyliminemethylpyrrolyl) manganese (II);
(2-Methylallyl)(2-isopropyliminemethylpyrrolyl) manganese (II);
(2-Methylallyl)(2-npropyliminemethylpyrrolyl) manganese (II);
(2-Methylallyl)(2-nbutyliminemethylpyrrolyl) manganese (II);
(2-Methylallyl)(2-secbutyliminemethylpyrrolyl) manganese (II);
(2-Methylallyl)(2-isobutyliminemethylpyrrolyl) manganese (II);
(2-Methylallyl)(2-tertbutyliminemethylpyrrolyl) manganese (II);
(2-Methylallyl)(2-trimethylsilylbutyliminemethylpyrrolyl) manganese (II);
(allyl)(2-iminemethylpyrrolyl) palladium(II);
(allyl)(2-methyliminemethylpyrrolyl) palladium (II);
(allyl)(2-ethyliminemethylpyrrolyl) palladium (II);
(allyl)(2-isopropyliminemethylpyrrolyl) palladium (II);
(allyl)(2-npropyliminemethylpyrrolyl) palladium (II);
(allyl)(2-nbutyliminemethylpyrrolyl) palladium (II);
(allyl)(2-secbutyliminemethylpyrrolyl) palladium (II);
(allyl)(2-isobutyliminemethylpyrrolyl) palladium (II);
(allyl)(2-tertbutyliminemethylpyrrolyl) palladium (II);
(allyl)(2-trimethylsilylbutyliminemethylpyrrolyl) palladium (II);
(1-Methylallyl)(2-iminemethylpyrrolyl) palladium (II);
(1-Methylallyl)(2-methyliminemethylpyrrolyl) palladium (II);
(1-Methylallyl)(2-ethyliminemethylpyrrolyl) palladium (II);
(1-Methylallyl)(2-isopropyliminemethylpyrrolyl) palladium (II);
(1-Methylallyl)(2-npropyliminemethylpyrrolyl) palladium (II);
(1-Methylallyl)(2-nbutyliminemethylpyrrolyl) palladium (II);
(1-Methylallyl)(2-secbutyliminemethylpyrrolyl) palladium (II);
(1-Methylallyl)(2-isobutyliminemethylpyrrolyl) palladium (II);
(1-Methylallyl)(2-tertbutyliminemethylpyrrolyl) palladium (II);
(1-Methylallyl)(2-trimethylsilylbutyliminemethylpyrrolyl) palladium (II);
(2-Methylallyl)(2-iminemethylpyrrolyl) palladium (II);
(2-Methylallyl)(2-methyliminemethylpyrrolyl) palladium (II);
(2-Methylallyl)(2-ethyliminemethylpyrrolyl) palladium (II);
(2-Methylallyl)(2-isopropyliminemethylpyrrolyl) palladium (II);
(2-Methylallyl)(2-npropyliminemethylpyrrolyl) palladium (II);
(2-Methylallyl)(2-nbutyliminemethylpyrrolyl) palladium (II);
(2-Methylallyl)(2-secbutyliminemethylpyrrolyl) palladium (II);
(2-Methylallyl)(2-isobutyliminemethylpyrrolyl) palladium (II);
(2-Methylallyl)(2-tertbutyliminemethylpyrrolyl) palladium (II); and
(2-Methylallyl)(2-trimethylsilylbutyliminemethylpyrrolyl) palladium (II).

3. The metal-containing precursor of claim 2, wherein the metal-containing precursor is 2-methylallyl 2-isopropyliminemethylpyrrolyl nickel(II).

4. The metal-containing precursor of claim 1, wherein the metal-containing precursor is (2-Methylallyl)(2-isopropyliminemethylpyrrolyl) nickel(II).

5. The metal-containing precursor of claim 1, wherein the metal-containing precursor is (allyl)(2-isopropyliminemethylpyrrolyl) nickel(II).

6. The metal-containing precursor of claim 1, wherein the metal-containing precursor is (2-methylallyl)(2-isopropyliminemethylpyrrolyl) cobalt (II).

7. The metal-containing precursor of claim 1, wherein the metal-containing precursor is (2-methylallyl)(2-isopropyliminemethylpyrrolyl) manganese (II).

8. A process for the deposition of a metal-containing film on a substrate, comprising the steps of:
introducing at least one metal-containing precursor into a reactor having at least one substrate disposed therein, the at least one metal-containing precursor having the formula:

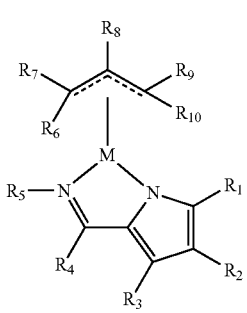

Compound (I)

wherein
M is a metal selected from the group consisting of Ni, Co, Mn, and Pd; and
each of $R_1$, $R_2$, $R_3$, $R_4$, $R_5$, $R_6$, $R_7$, $R_8$, $R_9$, and $R_{10}$ are independently selected from H; a C1-C4 linear, branched, or cyclic alkyl group; a C1-C4 linear, branched, or cyclic alkylsilyl group (mono, bis, or tris alkyl); a C1-C4 linear, branched, or cyclic alkylamino group; or a C1-C4 linear, branched, or cyclic fluoroalkyl group; and
depositing at least part of the metal-containing precursor onto the at least one substrate to form a metal-containing film.

9. The process of claim 8, further comprising introducing at least one reactant into the reactor.

10. The process of claim 9, wherein the reactant is selected from the group consisting of $H_2$, $NH_3$, $SiH_4$, $Si_2H_6$, $Si_3H_8$, $SiH_2Me_2$, $SiH_2Et_2$, $N(SiH_3)_3$, hydrogen radicals thereof; and mixtures thereof.

11. The process of claim 9, wherein the reactant is selected from the group consisting of: $O_2$, $O_3$, $H_2O$, NO, $N_2O$, oxygen radicals thereof; and mixtures thereof.

12. The process of claim 9, wherein the metal-containing precursor and the reactant are introduced into the reactor substantially simultaneously and the reactor is configured for chemical vapor deposition.

13. The process of claim 12, wherein the reactor is configured for plasma enhanced chemical vapor deposition.

14. The process of claim 9, wherein the metal-containing precursor and the reactant are introduced into the chamber sequentially and the reactor is configured for atomic layer deposition.

15. The process of claim 14, wherein the reactor is configured for plasma enhanced atomic layer deposition.

16. The process of claim 8, wherein the metal-containing precursor is selected from the group consisting of:
(allyl)(2-iminemethylpyrrolyl) nickel(II);
(allyl)(2-methyliminemethylpyrrolyl) nickel (II);
(allyl)(2-ethyliminemethylpyrrolyl) nickel (II);
(allyl)(2-isopropyliminemethylpyrrolyl) nickel(II);
(allyl)(2-npropyliminemethylpyrrolyl) nickel (II);
(allyl)(2-nbutyliminemethylpyrrolyl) nickel (II);
(allyl)(2-secbutyliminemethylpyrrolyl) nickel (II);
(allyl)(2-isobutyliminemethylpyrrolyl) nickel (II);
(allyl)(2-tertbutyliminemethylpyrrolyl) nickel (II);
(allyl)(2-trimethylsilylbutyliminemethylpyrrolyl) nickel (II);
(1-Methylallyl)(2-iminemethylpyrrolyl) nickel(II);
(1-Methylallyl)(2-methyliminemethylpyrrolyl) nickel (II);
(1-Methylallyl)(2-ethyliminemethylpyrrolyl) nickel (II);
(1-Methylallyl)(2-isopropyliminemethylpyrrolyl) nickel (II);
(1-Methylallyl)(2-npropyliminemethylpyrrolyl) nickel (II);
(1-Methylallyl)(2-nbutyliminemethylpyrrolyl) nickel (II);
(1-Methylallyl)(2-secbutyliminemethylpyrrolyl) nickel (II);
(1-Methylallyl)(2-isobutyliminemethylpyrrolyl) nickel (II);
(1-Methylallyl)(2-tertbutyliminemethylpyrrolyl) nickel (II);
(1-Methylallyl)(2-trimethylsilylbutyliminemethylpyrrolyl) nickel (II);
(2-Methylallyl)(2-iminemethylpyrrolyl) nickel(II);
(2-Methylallyl)(2-methyliminemethylpyrrolyl) nickel (II);
(2-Methylallyl)(2-ethyliminemethylpyrrolyl) nickel (II);
(2-Methylallyl)(2-isopropyliminemethylpyrrolyl) nickel (II);
(2-Methylallyl)(2-npropyliminemethylpyrrolyl) nickel (II);
(2-Methylallyl)(2-nbutyliminemethylpyrrolyl) nickel (II);
(2-Methylallyl)(2-secbutyliminemethylpyrrolyl) nickel (II);
(2-Methylallyl)(2-isobutyliminemethylpyrrolyl) nickel (II);
(2-Methylallyl)(2-tertbutyliminemethylpyrrolyl) nickel (II);
(2-Methylallyl)(2-trimethylsilylbutyliminemethylpyrrolyl) nickel (II);
(allyl)(2-iminemethylpyrrolyl) cobalt(II);
(allyl)(2-methyliminemethylpyrrolyl) cobalt (II);
(allyl)(2-ethyliminemethylpyrrolyl) cobalt (II);
(allyl)(2-isopropyliminemethylpyrrolyl) cobalt (II);
(allyl)(2-npropyliminemethylpyrrolyl) cobalt (II);
(allyl)(2-nbutyliminemethylpyrrolyl) cobalt (II);
(allyl)(2-secbutyliminemethylpyrrolyl) cobalt (II);
(allyl)(2-isobutyliminemethylpyrrolyl) cobalt (II);
(allyl)(2-tertbutyliminemethylpyrrolyl) cobalt (II);
(allyl)(2-trimethylsilylbutyliminemethylpyrrolyl) cobalt (II);
(1-Methylallyl)(2-iminemethylpyrrolyl) cobalt (II);
(1-Methylallyl)(2-methyliminemethylpyrrolyl) cobalt (II);
(1-Methylallyl)(2-ethyliminemethylpyrrolyl) cobalt (II);
(1-Methylallyl)(2-isopropyliminemethylpyrrolyl) cobalt (II);
(1-Methylallyl)(2-npropyliminemethylpyrrolyl) cobalt (II);
(1-Methylallyl)(2-nbutyliminemethylpyrrolyl) cobalt (II);
(1-Methylallyl)(2-secbutyliminemethylpyrrolyl) cobalt (II);
(1-Methylallyl)(2-isobutyliminemethylpyrrolyl) cobalt (II);
(1-Methylallyl)(2-tertbutyliminemethylpyrrolyl) cobalt (II);
(1-Methylallyl)(2-trimethylsilylbutyliminemethylpyrrolyl) cobalt (II);
(2-Methylallyl)(2-iminemethylpyrrolyl) cobalt (II);
(2-Methylallyl)(2-methyliminemethylpyrrolyl) cobalt (II);

(2-Methylallyl)(2-ethyliminemethylpyrrolyl) cobalt (II);
(2-Methylallyl)(2-isopropyliminemethylpyrrolyl) cobalt (II);
(2-Methylallyl)(2-npropyliminemethylpyrrolyl) cobalt (II);
(2-Methylallyl)(2-nbutyliminemethylpyrrolyl) cobalt (II);
(2-Methylallyl)(2-secbutyliminemethylpyrrolyl) cobalt (II);
(2-Methylallyl)(2-isobutyliminemethylpyrrolyl) cobalt (II);
(2-Methylallyl)(2-tertbutyliminemethylpyrrolyl) cobalt (II);
(2-Methylallyl)(2-trimethylsilylbutyliminemethylpyrrolyl) cobalt (II);
(allyl)(2-iminemethylpyrrolyl) manganese(II);
(allyl)(2-methyliminemethylpyrrolyl) manganese (II);
(allyl)(2-ethyliminemethylpyrrolyl) manganese (II);
(allyl)(2-isopropyliminemethylpyrrolyl) manganese (II);
(allyl)(2-npropyliminemethylpyrrolyl) manganese (II);
(allyl)(2-nbutyliminemethylpyrrolyl) manganese (II);
(allyl)(2-secbutyliminemethylpyrrolyl) manganese (II);
(allyl)(2-isobutyliminemethylpyrrolyl) manganese (II);
(allyl)(2-tertbutyliminemethylpyrrolyl) manganese (II);
(allyl)(2-trimethylsilylbutyliminemethylpyrrolyl) manganese (II);
(1-Methylallyl)(2-iminemethylpyrrolyl) manganese (II);
(1-Methylallyl)(2-methyliminemethylpyrrolyl) manganese (II);
(1-Methylallyl)(2-ethyliminemethylpyrrolyl) manganese (II);
(1-Methylallyl)(2-isopropyliminemethylpyrrolyl) manganese (II);
(1-Methylallyl)(2-npropyliminemethylpyrrolyl) manganese (II);
(1-Methylallyl)(2-nbutyliminemethylpyrrolyl) manganese (II);
(1-Methylallyl)(2-secbutyliminemethylpyrrolyl) manganese (II);
(1-Methylallyl)(2-isobutyliminemethylpyrrolyl) manganese (II);
(1-Methylallyl)(2-tertbutyliminemethylpyrrolyl) manganese (II);
(1-Methylallyl)(2-trimethylsilylbutyliminemethylpyrrolyl) manganese (II);
(2-Methylallyl)(2-iminemethylpyrrolyl) manganese (II);
(2-Methylallyl)(2-methyliminemethylpyrrolyl) manganese (II);
(2-Methylallyl)(2-ethyliminemethylpyrrolyl) manganese (II);
(2-Methylallyl)(2-isopropyliminemethylpyrrolyl) manganese (II);
(2-Methylallyl)(2-npropyliminemethylpyrrolyl) manganese (II);
(2-Methylallyl)(2-nbutyliminemethylpyrrolyl) manganese (II);
(2-Methylallyl)(2-secbutyliminemethylpyrrolyl) manganese (II);
(2-Methylallyl)(2-isobutyliminemethylpyrrolyl) manganese (II);
(2-Methylallyl)(2-tertbutyliminemethylpyrrolyl) manganese (II);
(2-Methylallyl)(2-trimethylsilylbutyliminemethylpyrrolyl) manganese (II);
(allyl)(2-iminemethylpyrrolyl) palladium(II);
(allyl)(2-methyliminemethylpyrrolyl) palladium (II);
(allyl)(2-ethyliminemethylpyrrolyl) palladium (II);
(allyl)(2-isopropyliminemethylpyrrolyl) palladium (II);
(allyl)(2-npropyliminemethylpyrrolyl) palladium (II);
(allyl)(2-nbutyliminemethylpyrrolyl) palladium (II);
(allyl)(2-secbutyliminemethylpyrrolyl) palladium (II);
(allyl)(2-isobutyliminemethylpyrrolyl) palladium (II);
(allyl)(2-tertbutyliminemethylpyrrolyl) palladium (II);
(allyl)(2-trimethylsilylbutyliminemethylpyrrolyl) palladium (II);
(1-Methylallyl)(2-iminemethylpyrrolyl) palladium (II);
(1-Methylallyl)(2-methyliminemethylpyrrolyl) palladium (II);
(1-Methylallyl)(2-ethyliminemethylpyrrolyl) palladium (II);
(1-Methylallyl)(2-isopropyliminemethylpyrrolyl) palladium (II);
(1-Methylallyl)(2-npropyliminemethylpyrrolyl) palladium (II);
(1-Methylallyl)(2-nbutyliminemethylpyrrolyl) palladium (II);
(1-Methylallyl)(2-secbutyliminemethylpyrrolyl) palladium (II);
(1-Methylallyl)(2-isobutyliminemethylpyrrolyl) palladium (II);
(1-Methylallyl)(2-tertbutyliminemethylpyrrolyl) palladium (II);
(1-Methylallyl)(2-trimethylsilylbutyliminemethylpyrrolyl) palladium (II);
(2-Methylallyl)(2-iminemethylpyrrolyl) palladium (II);
(2-Methylallyl)(2-methyliminemethylpyrrolyl) palladium (II);
(2-Methylallyl)(2-ethyliminemethylpyrrolyl) palladium (II);
(2-Methylallyl)(2-isopropyliminemethylpyrrolyl) palladium (II);
(2-Methylallyl)(2-npropyliminemethylpyrrolyl) palladium (II);
(2-Methylallyl)(2-nbutyliminemethylpyrrolyl) palladium (II);
(2-Methylallyl)(2-secbutyliminemethylpyrrolyl) palladium (II);
(2-Methylallyl)(2-isobutyliminemethylpyrrolyl) palladium (II);
(2-Methylallyl)(2-tertbutyliminemethylpyrrolyl) palladium (II); and
(2-Methylallyl)(2-trimethylsilylbutyliminemethylpyrrolyl) palladium (II).

17. The process of claim 8, wherein the metal-containing precursor is (2-Methylallyl)(2-isopropyliminemethylpyrrolyl) nickel(II).

18. The process of claim 8, wherein the metal-containing precursor is (allyl)(2-isopropyliminemethylpyrrolyl) nickel (II).

19. The process of claim 8, wherein the metal-containing precursor is (2-Methylallyl)(2-isopropyliminemethylpyrrolyl) cobalt (II).

20. The process of claim 8, wherein the metal-containing precursor is (2-Methylallyl)(2-isopropyliminemethylpyrrolyl) manganese (II).

* * * * *